(12) United States Patent
Mohammad

(10) Patent No.: US 6,669,671 B1
(45) Date of Patent: *Dec. 30, 2003

(54) RETRACTABLE NEEDLE WITH DUAL LOCKING MECHANISMS

(76) Inventor: Owais Mohammad, 5004 Rittenhouse St., Riverdale, MD (US) 20737

( * ) Notice: Subject to any disclaimer, the term of this patent is extended or adjusted under 35 U.S.C. 154(b) by 286 days.

This patent is subject to a terminal disclaimer.

(21) Appl. No.: 09/613,753

(22) Filed: Jul. 11, 2000

Related U.S. Application Data

(63) Continuation-in-part of application No. 09/218,040, filed on Dec. 22, 1998, and a continuation-in-part of application No. 09/316,047, filed on May 21, 1999, and a continuation-in-part of application No. 09/471,094, filed on Dec. 23, 1999.

(51) Int. Cl.[7] .............................................. A61M 5/32
(52) U.S. Cl. ...................................... 604/195; 604/196
(58) Field of Search .............................. 604/195, 196, 604/115, 181, 187, 190, 191, 192, 198, 110, 218, 197, 263, 200, 201, 204–206, 232, 244, 88, 82, 81

(56) References Cited

U.S. PATENT DOCUMENTS

| | | |
|---|---|---|
| 3,134,380 A | 5/1964 | Armao |
| 3,892,237 A | 7/1975 | Steiner |
| 4,416,663 A | 11/1983 | Hall |
| 4,425,120 A | 1/1984 | Sampson |
| 4,564,054 A | 1/1986 | Gustavsson |
| 4,639,249 A | 1/1987 | Larson |
| 4,664,654 A | 5/1987 | Strauss |
| 4,725,267 A | 2/1988 | Vaillancourt |
| 4,735,618 A | 4/1988 | Hagen |
| 4,737,150 A | 4/1988 | Baeumle et al. |
| 4,758,231 A | 7/1988 | Haber et al. |
| 4,772,272 A | 9/1988 | McFarland |
| 4,795,432 A | 1/1989 | Karczmer |
| 4,804,371 A | 2/1989 | Vallancourt |
| 4,816,022 A | 3/1989 | Poncy |
| 4,838,863 A | 6/1989 | Allard et al. |
| 4,842,587 A | 6/1989 | Poncy |
| 4,846,809 A | 7/1989 | Sims |
| 4,863,436 A | 9/1989 | Glick |
| 4,887,998 A | 12/1989 | Martin et al. |
| 4,900,307 A | 2/1990 | Kulli |

(List continued on next page.)

*Primary Examiner*—Sang Paik
*Assistant Examiner*—Vinod D. Patel
(74) *Attorney, Agent, or Firm*—Jones, Tullar & Cooper, P.C.

(57) ABSTRACT

A retractable syringe needle comprising a needle assembly including: a needle-holding mechanism comprising a hub and an annular sleeve connected with said hub; a hypodermic needle extending through said hub; and a pin directly connected to the exterior surface of said annular sleeve; a container having a tubular wall with a longitudinal slot therein, said container having a first open end adapted to receive a syringe barrel and a second open end adapted to admit a syringe needle, said container having said needle assembly mounted therein so that the pin is slidably engaged by the longitudinal slot, so that said needle assembly may be moved from a first position where the needle is within the container to a second position where the needle is exposed by sliding the pin toward the second open end of the container and causing the needle to pass through the second open end; a means for biasing the needle assembly toward said first position; and a means for releasably engaging the pin at a defined location in said longitudinal slot so as to hold said needle assembly in said second position; wherein said means for releasably engaging the pin comprises a notch which intersects said longitudinal slot at said defined location, so that said needle assembly may be releasably held in said second position by sliding said pin out of said longitudinal slot into said notch.

42 Claims, 24 Drawing Sheets

U.S. PATENT DOCUMENTS

| | | |
|---|---|---|
| 4,900,311 A | 2/1990 | Stern et al. |
| 4,915,697 A | 4/1990 | DuPont |
| 4,917,669 A | 4/1990 | Bonaldo |
| 4,917,673 A | 4/1990 | Coplin |
| 4,923,445 A | 5/1990 | Ryan |
| 4,927,416 A | 5/1990 | Tomkiel |
| 4,929,237 A | 5/1990 | Medway |
| 4,943,282 A | 7/1990 | Page et al. |
| 4,966,592 A | 10/1990 | Burns et al. |
| 4,998,924 A | 3/1991 | Ranford |
| 5,000,740 A | 3/1991 | Ducharme et al. |
| 5,011,475 A | 4/1991 | Olson |
| RE33,585 E | 5/1991 | Haber et al. |
| 5,086,780 A | 2/1992 | Schmitt |
| 5,088,986 A | 2/1992 | Nusbaum |
| 5,092,845 A | 3/1992 | Chang |
| 5,104,385 A | 4/1992 | Huband |
| 5,106,379 A | 4/1992 | Leap |
| 5,125,414 A | 6/1992 | Dysarz |
| RE34,045 E | 8/1992 | McFarland |
| 5,219,338 A | 6/1993 | Haworth |
| 5,222,947 A | 6/1993 | D'Amico |
| 5,232,456 A | 8/1993 | Gonzalez |
| 5,246,428 A | 9/1993 | Falknor |
| 5,254,100 A | 10/1993 | Huband |
| 5,279,579 A | 1/1994 | D'Amico |
| 5,290,255 A | 3/1994 | Vallelunga et al. |
| 5,323,456 A | 6/1994 | Oprea |
| 5,411,487 A | 5/1995 | Castagna |
| 5,423,758 A | 6/1995 | Shaw |
| 5,573,513 A | 11/1996 | Wozencroft |
| 5,591,138 A | 1/1997 | Vaillancourt |
| 5,695,474 A | 12/1997 | Daugherty |
| 5,695,475 A | 12/1997 | Best, Jr. et al. |
| 5,769,826 A | 6/1998 | Johnson et al. |
| 5,788,677 A | 8/1998 | Botich et al. |
| 6,162,197 A * | 12/2000 | Mohammad ................ 604/195 |

* cited by examiner

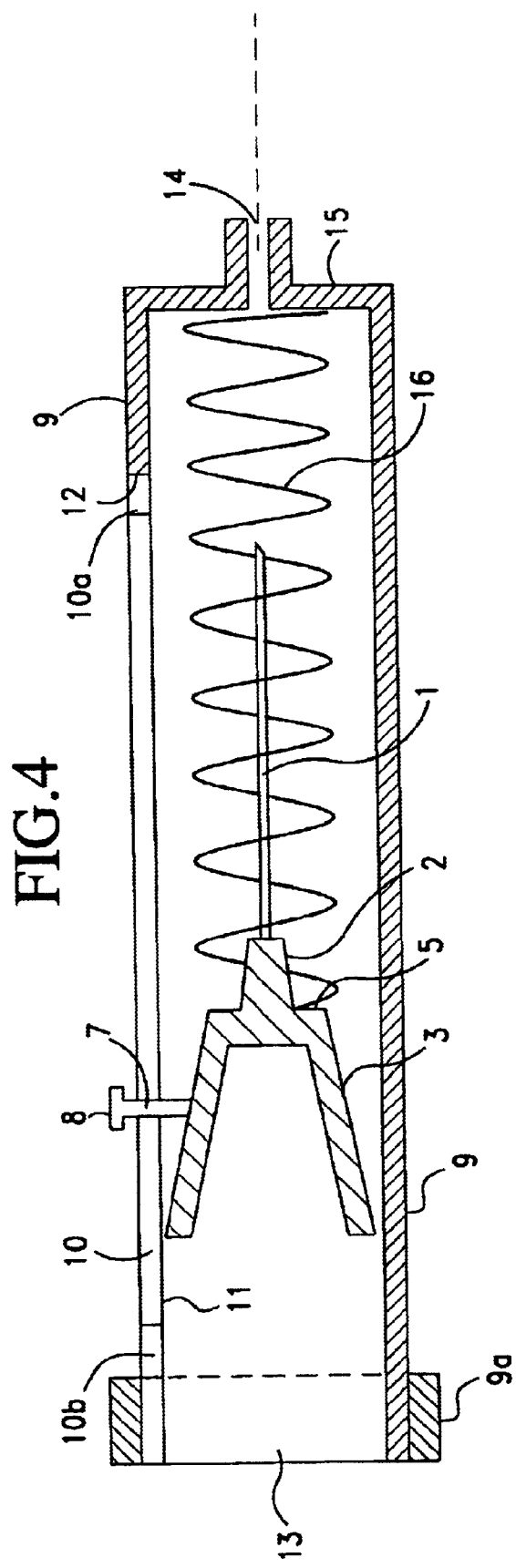

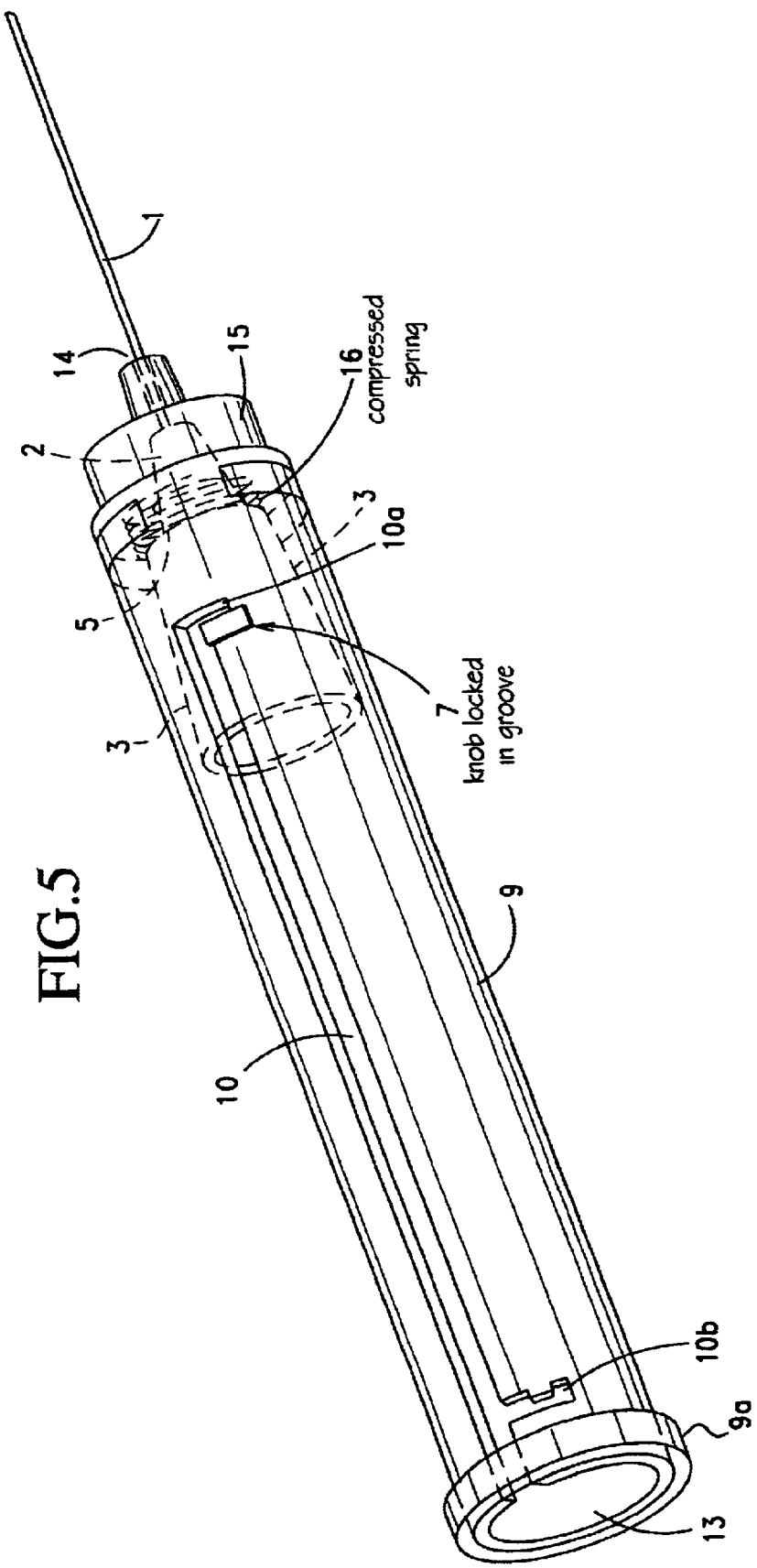

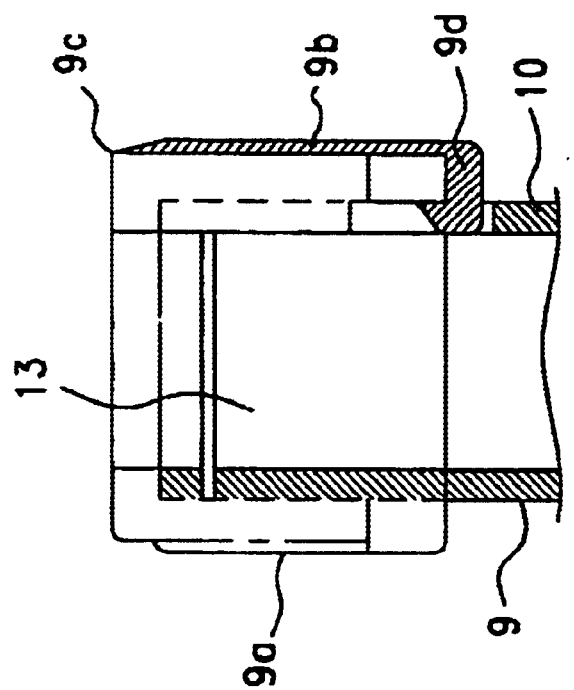
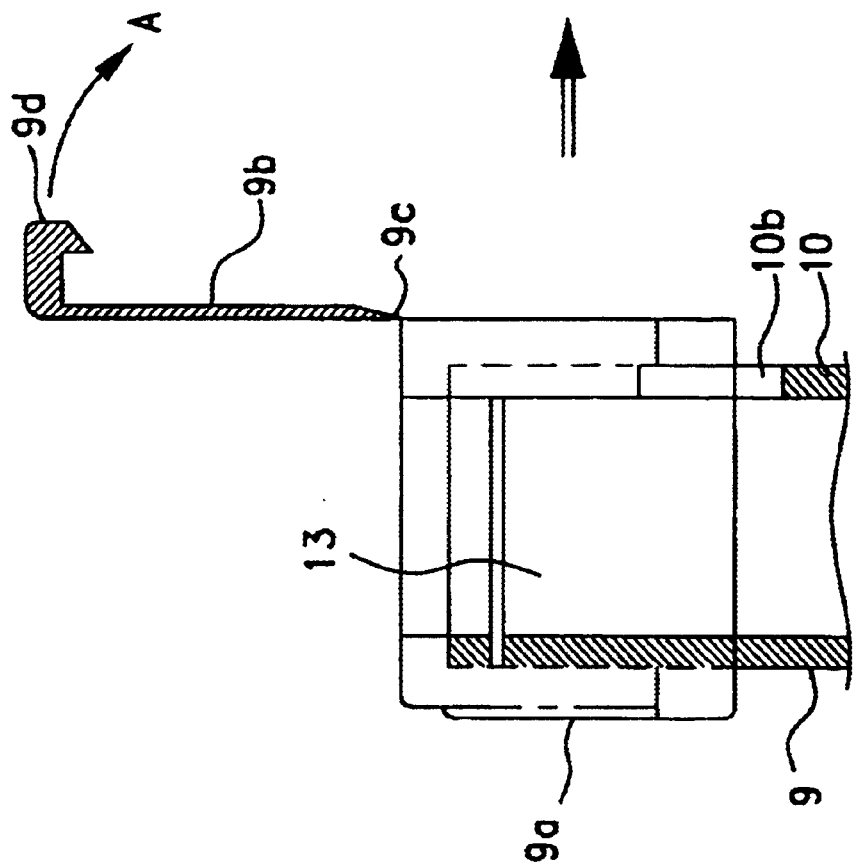
FIG.9b
FIG.9a

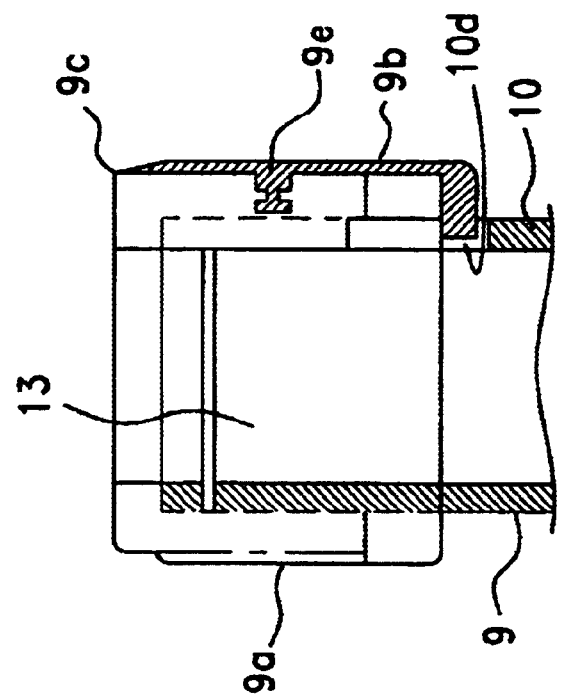
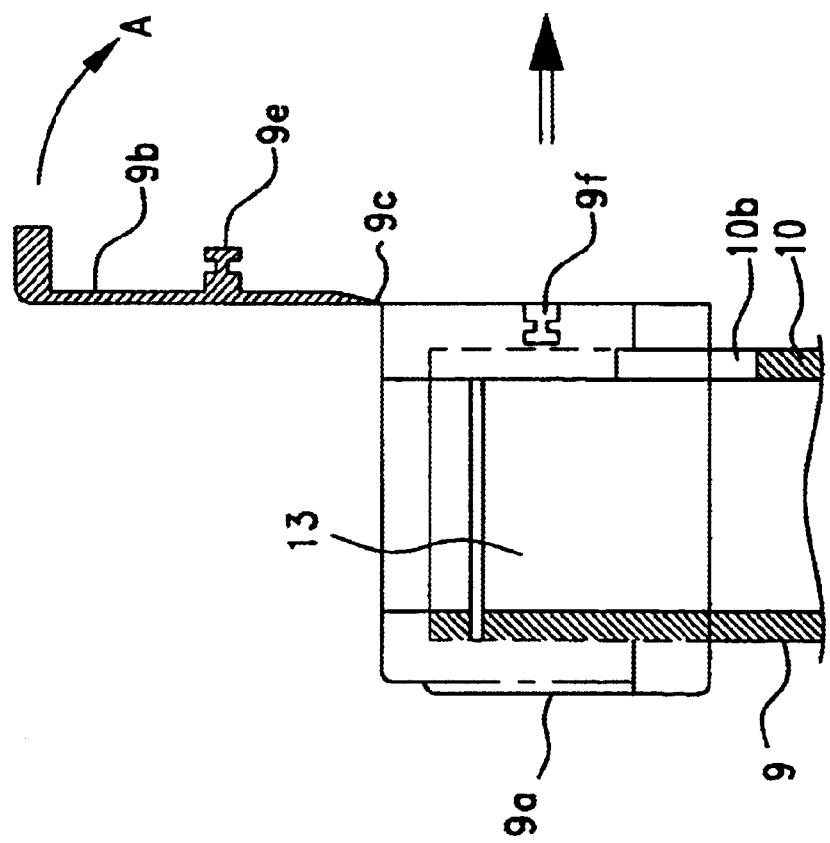

Grooved container in two pieces joined by threaded ends

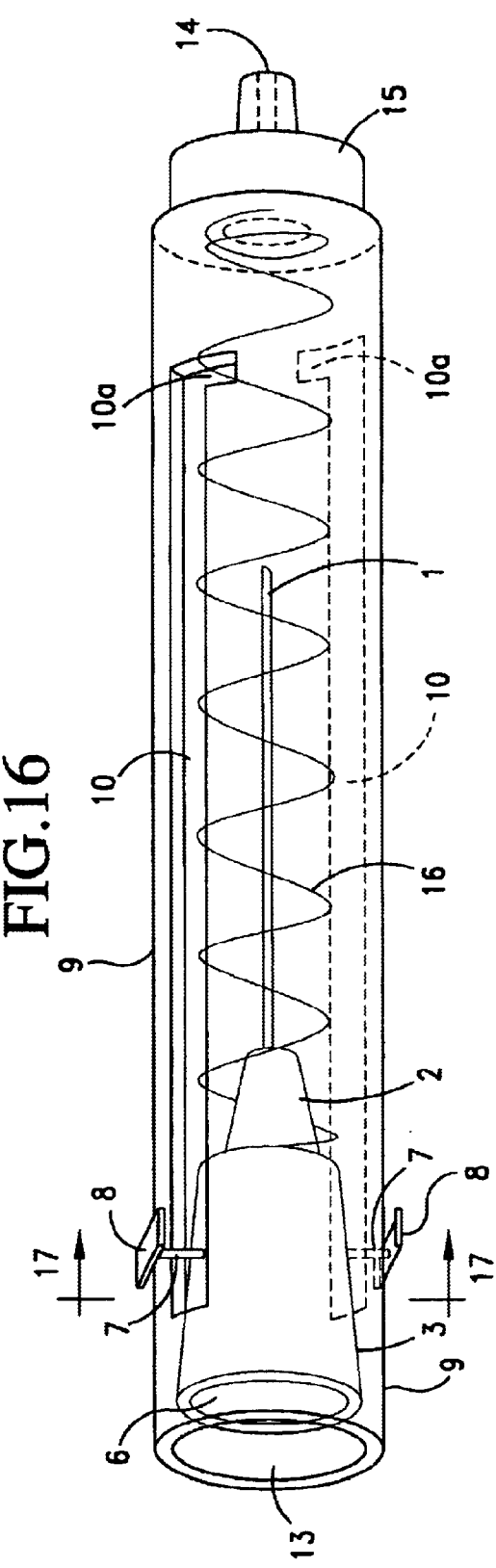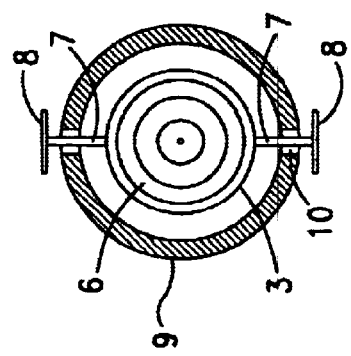

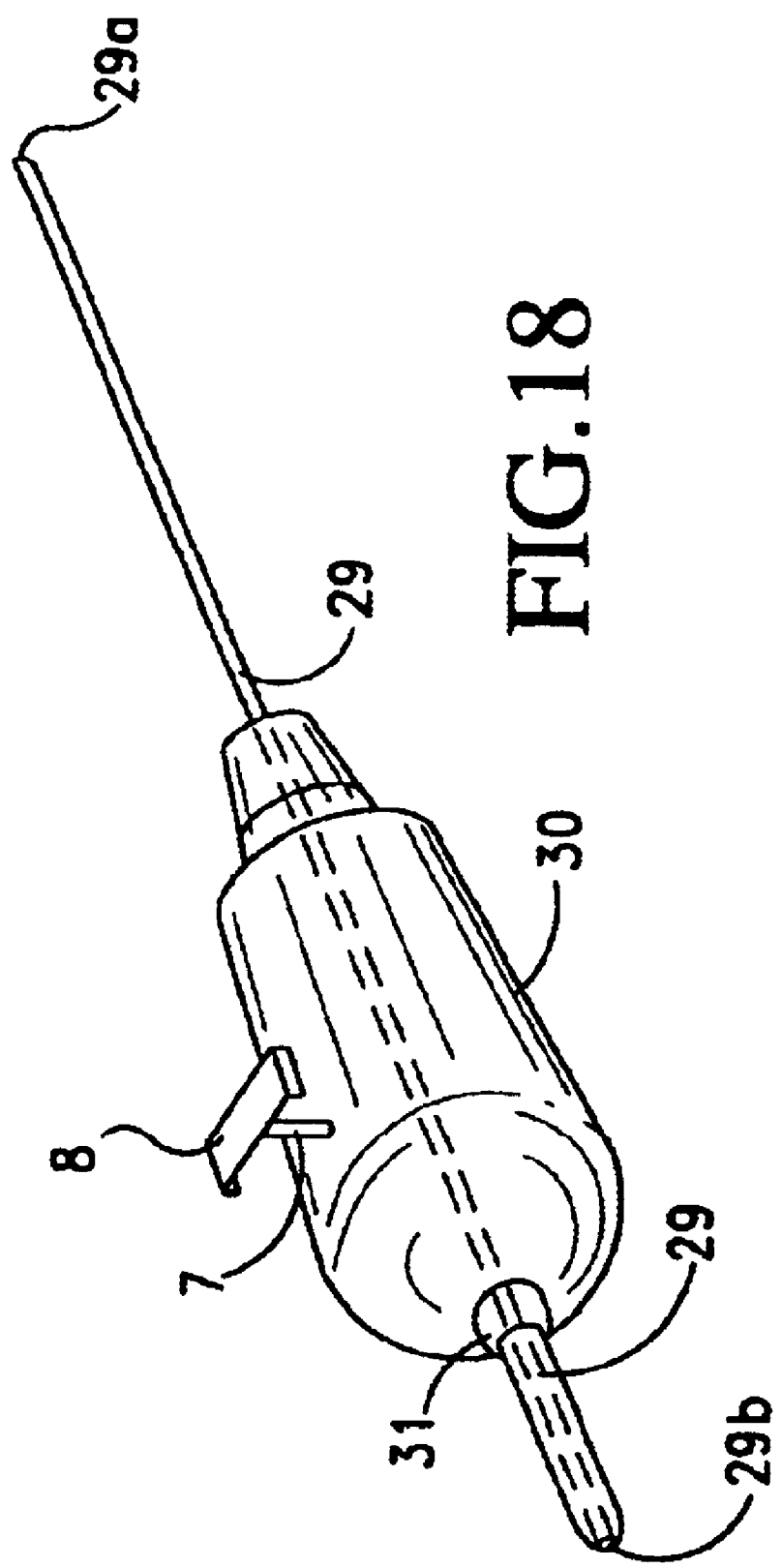

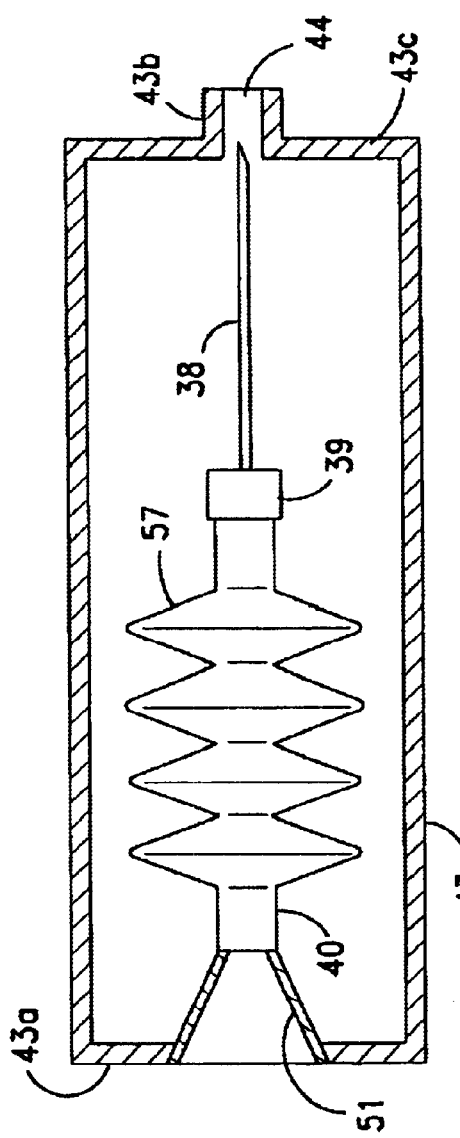
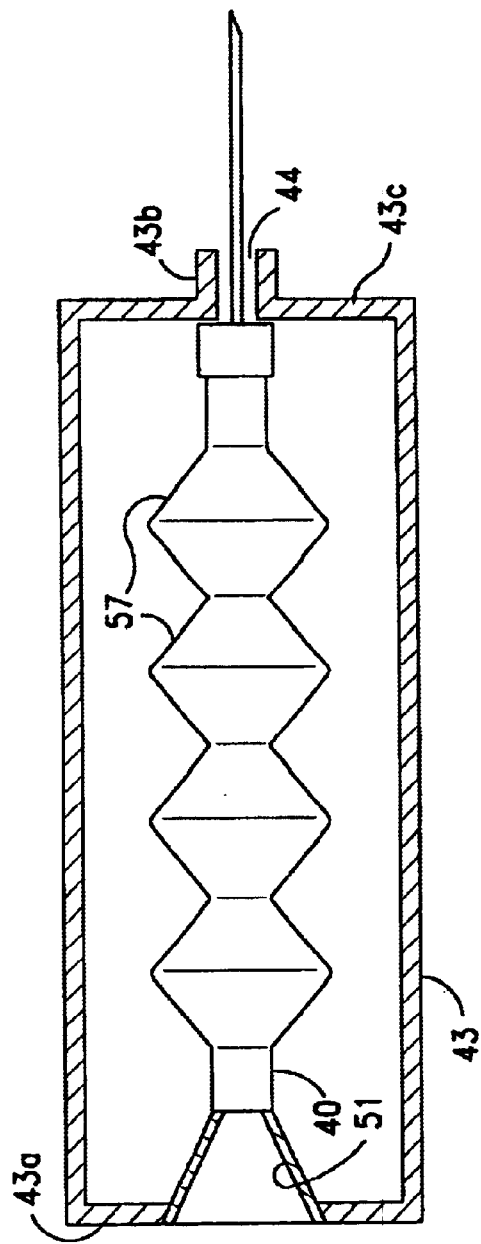
FIG.25a
FIG.25b

RETRACTABLE NEEDLE WITH DUAL LOCKING MECHANISMS

CONTINUATION INFORMATION

This application is a continuation-in-part of Ser. No. 09/218,040, filed Dec 22, 1998; Ser. No. 09/316,047, filed May 21, 1999; and Ser. No. 09/471,094, filed Dec. 23, 1999. The disclosure of each of the applications cited above is incorporated by reference herein.

BACKGROUND OF THE INVENTION

The present invention generally refers to hypodermic syringe needles for medical use. More particularly, the invention relates to hypodermic safety needles which retract into a container when not in use, preventing unintentional contact with the needle.

Prior art injection needles feature hollow needles which extend through a plastic hub. To prevent a user from accidentally pricking himself with the point of a needle, the needle is covered with a removable cover. Such covers frictionally engage the plastic hub, and may be readily removed once the needle is attached to a syringe barrel. After use, the cover may be reattached to the needle assembly, which is then separated from the syringe barrel and discarded. However, there is an unacceptable risk of accidental injury resulting from contact with the point of the needle during the recapping step. This is particularly dangerous as biological fluids contaminating the needle could enter the user's bloodstream. An improved means of covering a used injection needle is needed.

A wide variety of needles having a means for shielding a syringe needle from accidental contact with a user's fingers have been developed. For example, U.S. Pat. No. 4,900,311, "Hypodermic Syringe", issued to Stern on Feb. 13, 1990, relates to a hypodermic syringe having a syringe barrel, an injection needle attached to the syringe barrel, and a needle guard of elliptical cross section disposed around the syringe barrel. The needle guard may be moved from a first position which covers the needle to a second position which exposes the needle. When the guard is in the second position, tabs on the interior of the guard engage slots on the syringe barrel, locking the guard into position. When the tabs are released from the slots by squeezing the elliptical guard along its longitudinal axis, a spring causes the guard to move into the first position, hiding the needle. The entire syringe assembly is then discarded.

This device, while useful, does have certain drawbacks. The syringe barrel used with this assembly has a highly specialized structure; a generic syringe barrel cannot readily be substituted. Also, the syringe barrel cannot readily be sterilized and reused. No provision for separation of the needle from the syringe barrel without removing the syringe needle from the protective needle guard is provided. Finally, there is the risk of accidentally squeezing the elliptical needle guard, causing the spring to move the needle guard into a position which conceals the needle prior to use of the needle.

U.S. Pat. No. 4,664,654, "Automatic protracting and locking hypodermic needle guard", issued to Strauss on May 12, 1987, relates to a two-piece needle shield comprising a sliding member and a stationary member. A latch holds the sliding member in position. When the latch is released, a spring causes the sliding member to retract inside the stationary member, exposing the needle. However, this device causes the user to place his hand in proximity to the needle at the time it is exposed, increasing the likelihood of injury from accidental contact with the needle.

U.S. Pat. No. 5,246,428, "Needle Safety Mechanism", issued to Falknor on Sep. 21, 1993, relates to a needle safety mechanism comprising a base adapted to be fixed with respect to the needle, and a sheath which is movable between a first position which exposes the needle and a second position which covers the needle. A latch cooperative between the base and the sheath may be used to releasably latch the sheath in the position which covers the needle. A spring biases the sheath into the needle covering position. No mechanism for latching the sheath in a position which exposes the needle is provided, however. This may be an inconvenience for workers who wish to see the precise spot where they are administering an injection.

U.S. Pat. No. 5,279,579, "Self-recapping Injection Needle Assembly", issued to D'Amico on Jan. 18, 1994, relates to a self-capping injection needle assembly which includes a hub slidably positioned within a cylindrical cover adapted to receive a syringe barrel, and a needle mounted on the hub. A spring biases the hub into a position in which the needle is contained within the tubular cover. When the spring is compressed, the hub may slide into a position which exposes the needle. The hub includes a pin which slidably engages a longitudinal groove in the tubular cover. The groove includes a transverse leg adapted to receive the pin. When the pin is positioned in the transverse leg, the hub is releasably locked into a position which exposes the needle. The hub has a threaded female joint which may be screwed onto a syringe barrel having a corresponded threaded male joint. Different size tubular covers may be used for different size syringe barrels.

This device has certain disadvantages. First, in a medical environment time is often a critical factor. A more rapid method of affixing a needle to a syringe barrel than screwing it on is desirable. Also, only syringe barrels with a specific type of joint adapted to mate with the hub are usable with this device. Most commonly used medical syringe barrels have frusto-conical tips which frictionally engage syringe needle hubs having frusto-conical cavities therein; such commonly used barrels cannot be used with the threaded connections envisioned by D'Amico. D'Amico requires that a hub having a specific diameter must be used with a tubular cover having an inner diameter which is substantially equal to the hub diameter. Most commonly available syringe needle hubs have a single standard size, and cannot be used with a range of tubular cover sizes. Therefore, D'Amico's invention necessitates creation of a range of expensive and specialized syringe needles having a range of hub sizes. Also, since the diameter of D'Amico's hub is very nearly equal to the interior diameter of the tubular cover, it is difficult to insert a hub having a protruding pin into the cover. An easy method of assembling such a device is desirable.

There is a long-felt need in the art for a safety needle assembly having a retractable needle which may be easily assembled, and which may be used with commonly available syringe barrels having frusto-conical tips which frictionally engage a syringe needle assembly. The required safety needle assembly must also avoid the other disadvantages of known prior art devices. It is an object of this invention to provide such a safety needle assembly.

SUMMARY OF THE INVENTION

The present invention provides a disposable hypodermic syringe needle which retracts into a container for safe disposal. The container features a tubular wall having a longitudinal slot therethrough. One end of the container is open so that a syringe barrel may be received therein. The second end of the container has an opening which is sufficiently large to receive a hypodermic needle, but too small to receive a syringe barrel. A hypodermic needle assembly is contained within the container. This assembly features a hypodermic needle which is affixed to a hub. An annular sleeve defining a cavity surrounds the periphery of the hub. The cavity in the annular sleeve is designed to frictionally engage the tip of a syringe barrel. A spring engages the hub of the needle assembly and a ridge on the interior of the wall of the second end of the container. This spring biases the hub away from the second end of the container so that the needle attached to the hub is hidden within the container. When the spring is compressed, the needle is able to pass through the opening of the second end of the container. A pin attached to the annular sleeve is slidably engaged by the longitudinal slot in the container wall, holding the needle within the container while allowing it to slide back and forth. A knob mounted on the pin is positioned outside the container. The knob is too large to pass through the longitudinal slot, and acts to position the hub of the needle along the axis of the container. When the knob is pushed toward the second end of the container, the hub moves toward the second end of the container, compressing the spring and causing the needle to emerge through the second open end of the container. A means for reversibly engaging the knob when the spring is compressed is also provided. This allows the needle to be retained in an exposed position.

The needle may be frictionally secured to a syringe barrel having a plunger slidably mounted therein. More specifically, a syringe barrel having a tip is secured to the needle assembly by inserting the tip of the syringe barrel into the cavity of the annular sleeve until the barrel tip is frictionally secured to the barrel sleeve. Additional features of the invention will be described in the detailed description of the preferred embodiments. Any syringe barrel having an appropriately shaped tip may be used with the inventive needle assembly.

Other embodiments of this invention are contemplated. The needle assembly of this invention may be attached to an IV tube and used for intravenous administration of fluids. Also, a modified needle assembly having a double-ended hypodermic needle that is affixed to a hub may be used to withdraw samples of venous blood.

DESCRIPTION OF THE DRAWINGS

FIG. 1d illustrates an end view of the needle assembly of FIG. 1a.

FIGS. 2 and 3 show grooved containers designed to contain the needle of FIG. 1a.

FIG. 4 shows a retractable hypodermic safety needle within a container, with the needle in a retracted configuration.

FIG. 5 shows a retractable hypodermic safety needle within a container, with the needle in an exposed configuration.

FIGS. 7, 8a, 8b, 8c, 9a, 9b, and 10 show mechanisms to irreversibly lock a retractable needle in a retracted configuration.

FIGS. 16 and 17 show a second modified version of the apparatus of FIG. 4.

FIG. 18 shows a modified version of the needle assembly of FIG. 1a, for use in taking blood samples.

FIGS. 22, 25a, and 25b show a needle assembly featuring an adjustable-length tube.

DETAILED DESCRIPTION

The needle used in the present invention is designed for use with a syringe comprising a plunger and a syringe barrel having a tubular wall with a defined outer diameter, where the barrel has an open end adapted to receive the plunger and a closed end having a cylindrically symmetric tip projecting therefrom. The tip of the barrel has a defined diameter which is less than the defined outer diameter of the syringe barrel and a longitudinal bore passing through the tip and the closed end of the barrel.

Figure 1A:
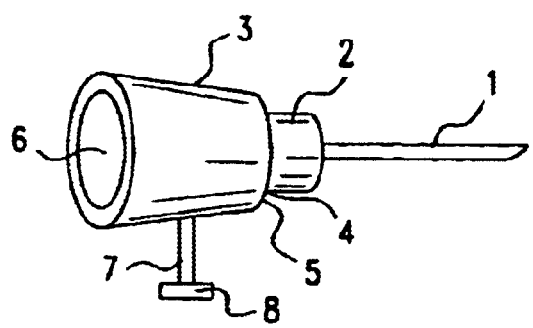
FIG. 1a illustrates a side view of a preferred needle assembly for use in the syringe assembly of this invention.
Figure 1B:
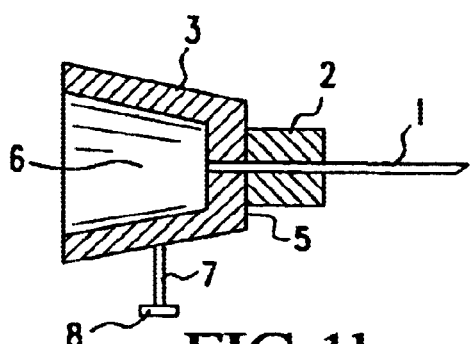
FIGS. 1b and 1c illustrate cross-sectional views of preferred needle assembly.
Figure 1C:
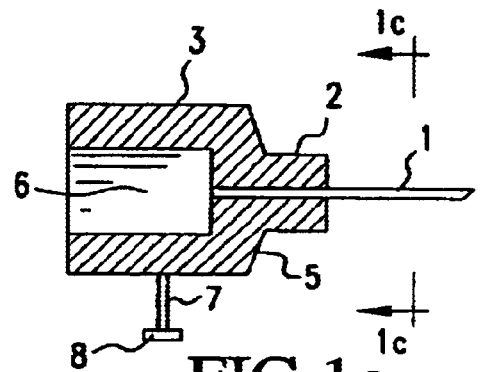

FIG. 1a illustrates a hypodermic needle for use in the syringe assembly of this invention. Needle 1 is affixed to hub 2. A hollow bore runs longitudinally through needle 1 and hub 2. An annular sleeve 3 is affixed to the outer periphery 4 of hub 2. A ledge 5 encircling hub 2 is defined by the edge of sleeve 3. Sleeve 3 defines a cavity 6 adapted to frictionally engage the tip of the syringe barrel, as shown in the cross-sectional views of FIGS. 1b and 1c. The diameter of cavity 6 is sized to match the diameter of the tip of the syringe barrel, while being substantially smaller than the diameter of the outer diameter of the tubular wall of the syringe barrel, allowing the cavity 6 to fit over the syringe barrel tip without extending over the external surface of the wall of the syringe barrel. In one preferred embodiment, the interior surface of the sleeve defines a frusto-conical cavity 6, where the sleeve is adapted to frictionally engage a frusto-conical tip of a syringe barrel (FIG. 1b). In another preferred embodiment, the interior surface of the sleeve defines a cylindrical cavity of constant diameter, where the sleeve is adapted to frictionally engage a cylindrical syringe barrel tip of constant diameter (FIG. 1c).

Figure 1D:
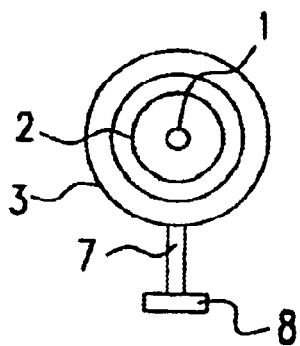

A pin 7 is affixed to the outer surface of sleeve 3. A thumbrest, knob or crosspiece 8 is mounted on pin 7. The crosspiece may take any of several forms. It may be square. It may also be a round disk, a spherical knob, or a hemispherical knob. It may also take the form of a ring which encircles hub 2, without being connected to hub 2, except by means of stem 7. Crosspiece 8 should be positioned so that, when viewed along the axis of needle 1, piece 8 and pin 7 intersect at a right angle (FIG. 1d). Although pin 7 and crosspiece 8 may be manufactured separately and secured together, it is preferred that 7 and 8 be manufactured as a single piece.

Figure 2:
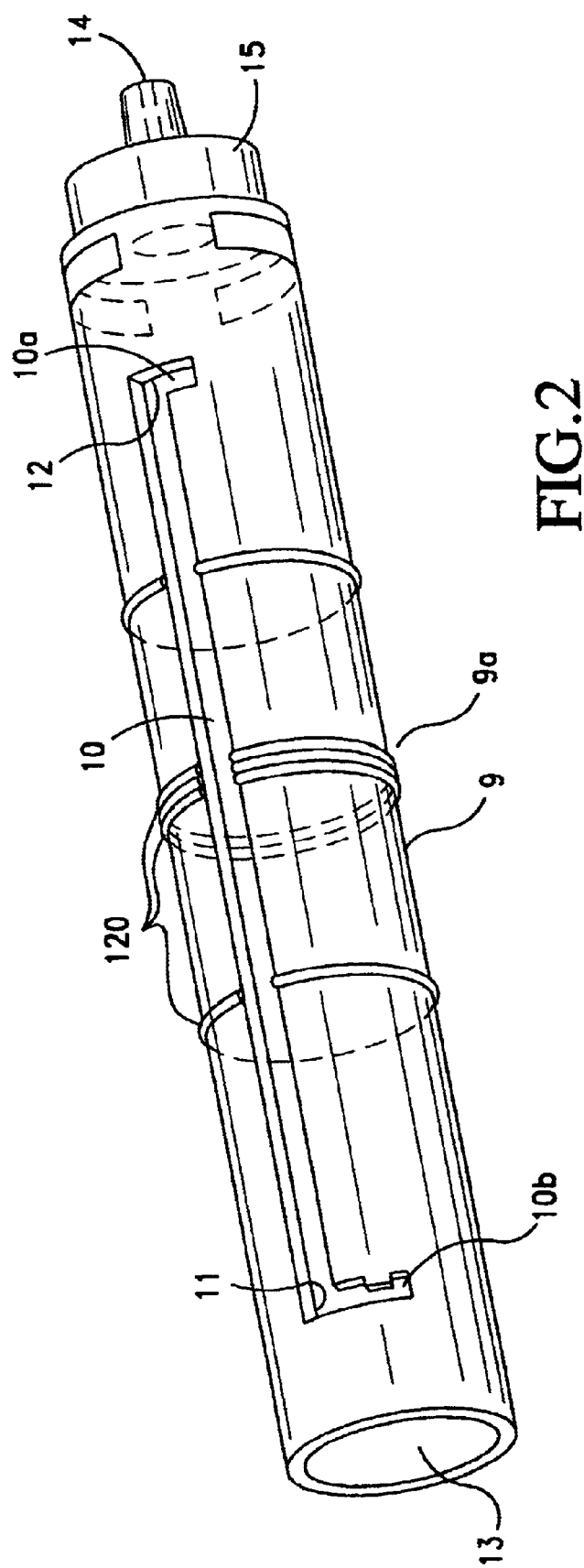

FIG. 2 shows a grooved container designed to house the needle of FIG. 1a. The container has a tubular wall 9 having a longitudinal slot 10 therethrough. A first end of the container has an opening 13 adapted to receive a syringe barrel. The second end of the container has an opening 14 which is large enough to allow needle 1 to pass therethrough, but too small to admit a syringe barrel or a human finger. A ledge 15 on the second end of the container runs from the interior of wall 9 to the edge of opening 14. Slot 10 runs from a point near the first end of the container, without reaching the first end of the container, to a point near the second end of the container, without reaching the second end of the container. A second slot 10a, running a part of the way around the circumference of wall 9, intersects slot 10 near the second end of the container. A similar slot 10b intersects slot 10 near the first end of the container. Slots 10a and 10b are preferably parallel to each other. A series of circumferential ridges 120 may optionally be positioned on the exterior of the container, said ridges being effective to strengthen the container, although this feature is not necessary for proper function of the invention.

Figure 3:
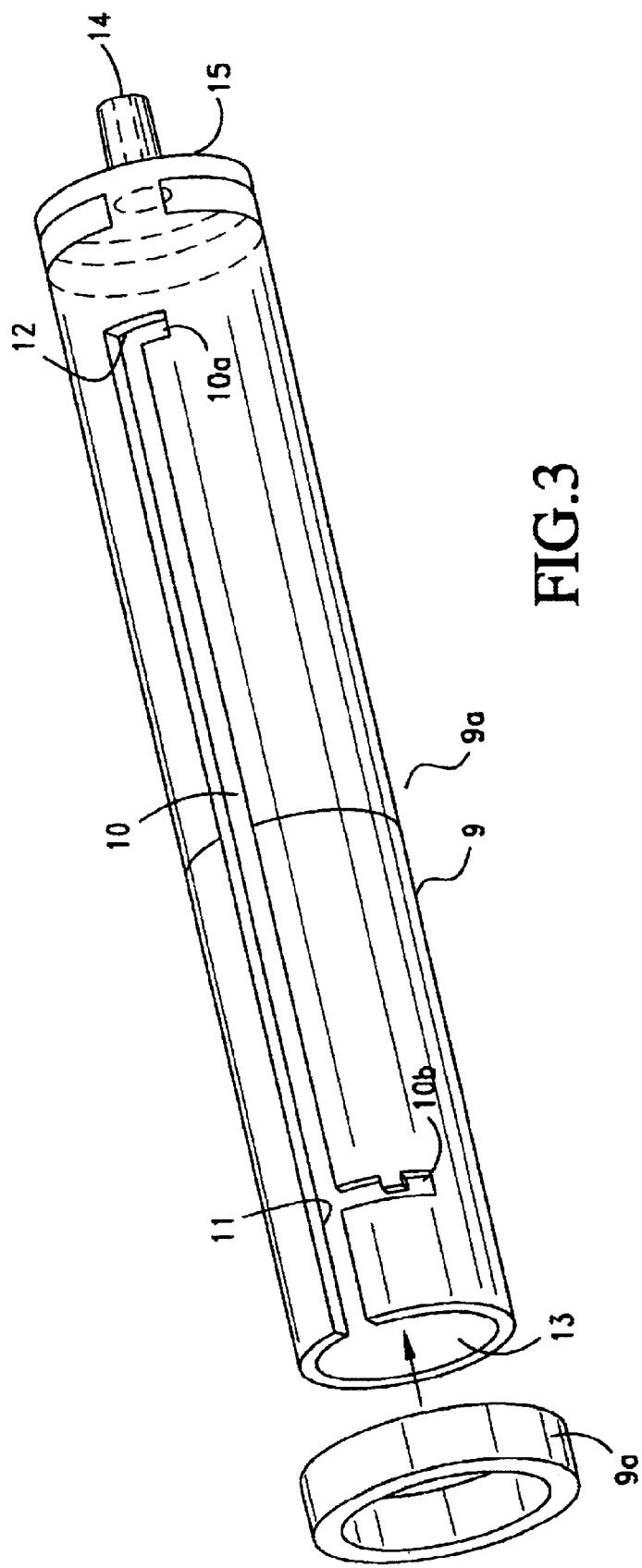
Figure 20:
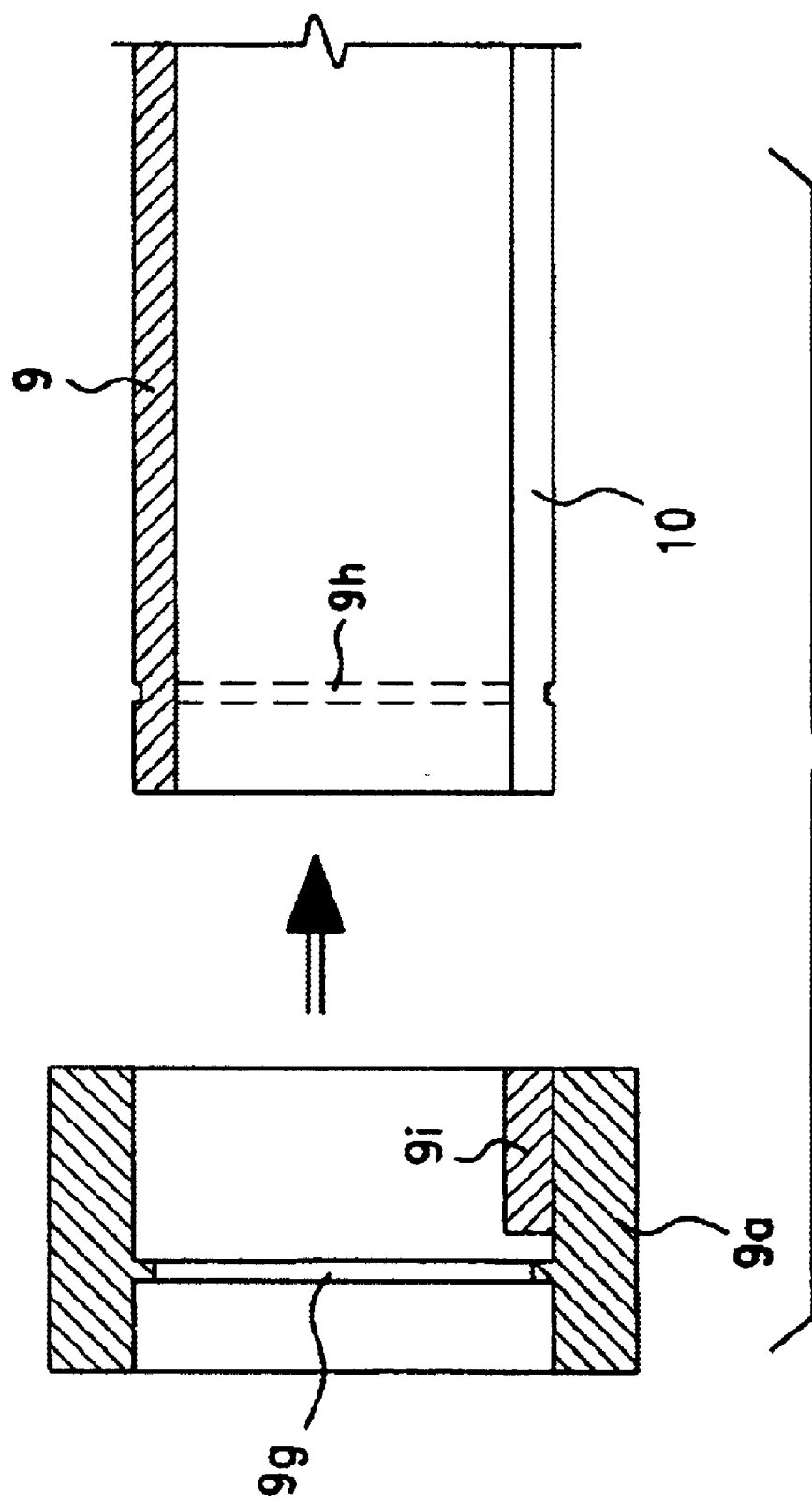
FIG. 20 shows how rigid ring 9a fits onto the tubular container of FIG. 2.

Although the container may be made in a single piece, it is preferred to manufacture the container in two pieces (FIG. 3). The first piece is a housing or a container having a tubular wall 9 with a longitudinal slot 10 therethrough, exactly as previously described; the sole difference is that the longitudinal slot 10 extends from the first open end of the container to a defined point near the second open end of the container, slot 10 being open-ended at the first open end of the container and closed at the second open end of the container discuss slots 10a & 10b. The second piece of the container is a rigid ring 9a having a first end and a second end, where the rigid ring 9a is positioned over the first open end of the container so as to close the open end of the longitudinal slot. Preferably, one end of the ring is flush with one edge of slot 10b without blocking slot 10b. To help hold the ring 9a in position on the wall 9 of the first piece of the container, the ring has a circumferential ridge on its interior surface, and the container has a circumferential groove on its exterior surface near the first open end of the container (FIG. 20). The rigid ring fits over the first open end of the container until the circumferential ridge snaps into the circumferential groove. Additionally, the rigid ring may have a longitudinal ridge on its interior surface, where the longitudinal ridge fits into the open end of the longitudinal slot so as to prevent the ring from rotating relative to the wall 9.

FIG. 4 shows how the needle assembly of FIG. 1a is contained within the container of FIG. 2. The needle assembly is positioned within the container with pin 7 slidably engaging slot 10. Crosspiece 8 helps to retain pin 7 within slot 10. Piece 8 is sufficiently large that it cannot pass through slot 10 into the interior of the container, and is rigidly secured to a defined position along the length of pin 7, where the defined position on pin 7 is chosen so that hub 2 of the needle assembly is positioned along the cylindrical axis of the container, as shown in the cross-sectional view of FIG. 4. More particularly, the distance between the axis of hypodermic needle 1 and crosspiece 8 is equal to the one half the external diameter of the wall 9 of the container. This retains needle 1 along the axis of the container. Removal of knob 8 would allow pin 7 to slip out of slot 10, causing hub 2 to fall against the inside of wall 9. Ring 9a prevents pin 7 from exiting the open end of slot 10. As shown in FIGS. 4, 9a is flush with one edge of slot 10a. In general, the size of the container can be chosen so as to accommodate any size syringe. Thus, if a large syringe is to be used, a container having a large interior diameter is required. The maximum diameter of the combination of hub 2 and sleeve 3 can be selected so as to correspond to the interior diameter of the container wall 9. Thus, a specific needle-holding assembly having a specific hub size may be manufactured for each commonly-used syringe size. Alternatively, a standard-sized hub and sleeve may be used in each case, regardless of the size of the syringe and/or container. This may be done by varying the length of pin 7, so as to match the distance between sleeve 3 and the wall 9 of the container.

A needle having a hub of any desired size may be used in a container having any desired radius without losing the desired axial orientation of needle 1 by simply changing the distance between the axis of needle 1 and crosspiece 8. This makes it unnecessary to manufacture a wide variety of needle hubs, with each needle hub being reserved for a different container size, as required by D'Amico.

A spring 16 is also positioned within the container, as shown in FIG. 4 A first end of spring 16 engages ledge 15 at the second end of container 1, while the second end of spring 16 engages ledge 5 encircling hub 2. The spring acts to bias hub 2 away from the second end of the container so that needle 1 is effectively concealed within the container. This allows the user to effectively handle the assembly without pricking his fingers. Preferably, the tip of the needle bore is positioned inside 14 (FIG. 4).

When one is ready to use the needle, needle 1 may be exposed by pushing hub 2 toward the second end of the container. This is most easily done by manually sliding crosspiece 8, attached to pin 7, along slot 10 with the user's thumb or finger. As hub 2 approaches the second end of the container, spring 16 is compressed and needle 1 passes through opening 14 in the container and is exposed. Since needle 1 is directed along the axis of the container, it is very easy to direct the needle through opening 14. When pin 7 reaches end 12 of slot 10, the needle is rotated by reversibly pushing pin 7 into slot 10a. Slot 10a acts as a stop, preventing spring 16 from decompressing and causing needle 1 to retract into the container. An illustration of the needle assembly in this configuration is shown in FIG. 5. This has the great advantage that one may expose a sheathed needle without having to position one's fingers near the needle itself, as is done when exposing the sheathed needle described by Strauss (vide supra). When it is desired to retract the needle, 16 reversibly pushes pin 7 along slot 10 pin 7 out of slot 10a, and then spring.

Figure 6C:
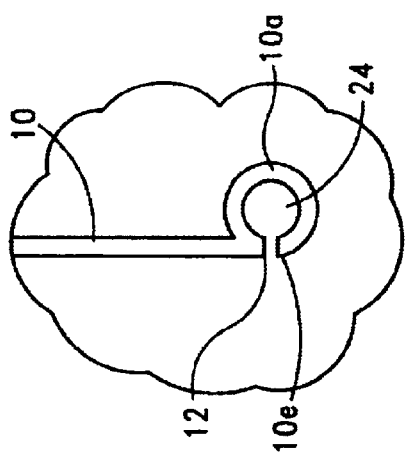
FIGS. 6a through 6c show various embodiments of locking mechanisms to hold a retractable needle in an exposed configuration.
Figure 6B:
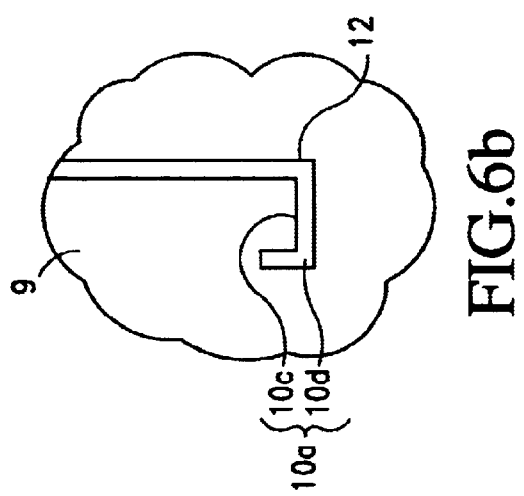
Figure 6A:
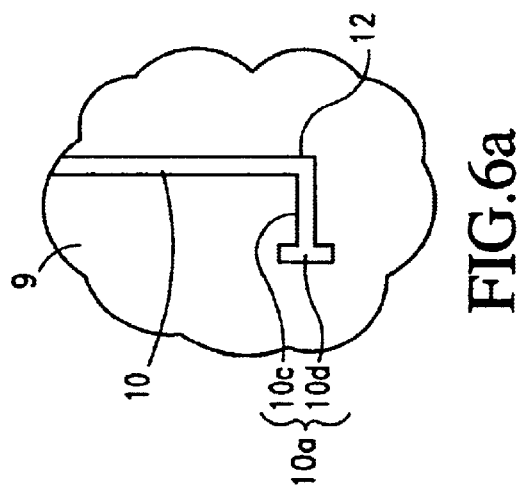

As shown in FIGS. 1 through 5, slot 10a is a simple transverse slot which intersects slot 10 at a right angle. While this is an effective arrangement, other configurations of slot 10a are possible. Three such arrangements are shown in FIGS. 6a through 6c. In FIG. 6a, slot 10a is configured as a T-shaped notch. This T-shaped notch comprises a first transverse leg 10d which intersects slot 10, and a second leg 10e which intersects the transverse leg and is substantially parallel to slot 10. If desired, transverse leg 10d and leg 10e may be configured as an L-shaped notch, as shown in FIG. 6b. The notches of FIGS. 6a and 6b operate in the following manner. Hub 2 is moved forward within the container until pin 7 reaches end 12 of slot 10. At this point, the needle is rotated by pushing pin 7 into transverse leg 10d of slot 10a until the pin reaches the point where legs 10d and 10e intersect. At this point, spring 16 biases the hub 2 away from ridge 15, causing pin 7 to enter leg 10e of slot 10a. Leg 10e acts as a stop, preventing spring 16 from decompressing further and causing needle 1 to retract into the container. Leg 10e also prevents the user from accidentally pushing pin 7 out of slot 10a.

In FIG. 6c, slot 10a is configured as a C-shaped slot, where a first end of the C-shaped slot intersects slot 10 at point 12, and a second end 10d lies in line with slot 10. The end of slot 10 is separated from the second end of slot 10a by tab 24. The C-shaped configuration of slot 10a operates in the following manner. Hub 2 is moved forward within the container until pin 7 reaches end 12 of slot 10. At this point, the needle is rotated by pushing pin 7 along slot 10a until it reaches end 10d. At this point, spring 16 biases the hub 2 away from ridge 15, pressing pin 7 against tab 24. Tab 24 acts as a stop, preventing spring 16 from decompressing further and causing needle 1 to retract into the container.

Notch 10b, which intersects longitudinal slot 10 near the first end of the container, also functions as a locking mechanism. When the needle is retracted into the container, pin 7 is adjacent to slot 10b. Pin 7 may then be pushed sideways into slot 10b so as to hold the needle assembly in the retracted position. Like slot 10a, slot 10b may be a straight transverse slot, a C-shaped slot, an L-shaped slot, or a T-shaped slot. Notches 10a and 10b are each wide enough to receive the pin engaged by the longitudinal slot. To retain pin 7 in notch 10a or in notch 10b when the needle is in use, each notch may be provided with teeth 200 which are spaced sufficiently closely together that the pin may not be pushed into, or out of, the notch without the deliberate application of force. A pair of such teeth are shown in the entrance to notch 10b in FIG. 7.

Figure 7:
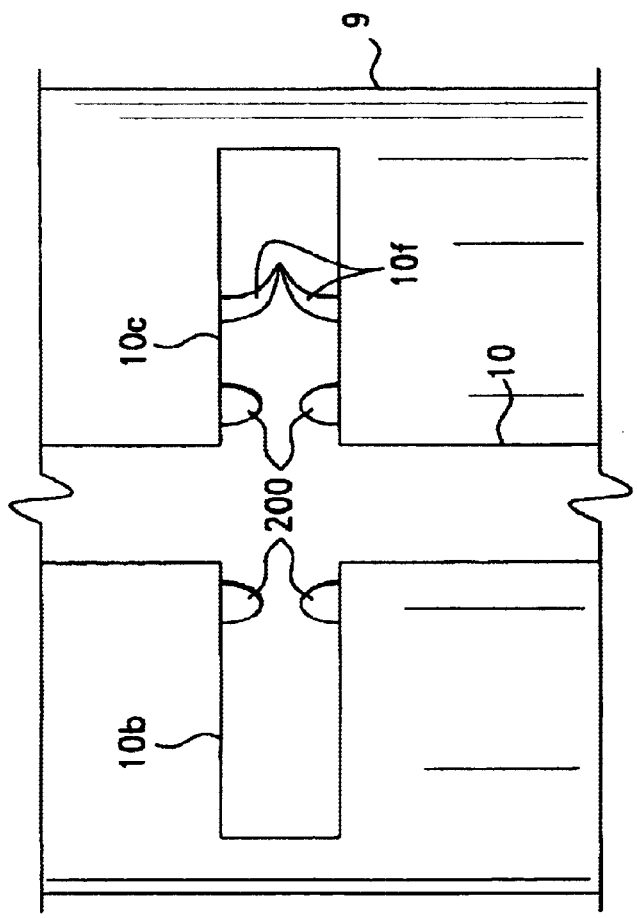

Preferably, since used syringe needles may be biohazards, the retractable syringe needle also includes a mechanism for irreversibly engaging the pin near the first end of the container so as to retain a used needle in the retracted position. One version of the irreversible locking mechanism comprises a third notch 10c which intersects longitudinal slot 10 so that slots 10b and 10c are collinear, extending from opposite sides of slot 10 (FIG. 7). Slot 10c is wide enough to receive the pin engaged by the longitudinal slot, and comprises a pair of flexible projections 10f extending from opposite sides of slot 10c. The projections have tips which contact each other, said tips being adapted to allow the pin engaged by the slot to pass therethrough when the pin enters the slot 10c from longitudinal slot 10, and to not allow the pin to pass therethrough to exit slot 10c. Each of the flexible projections makes an acute angle with the wall of slot 10c, and each of the flexible projections is directed away from the longitudinal slot 10. The pin 7 can pass between the projections as it enters slot 10c (FIG. 8b), but it cannot exit slot 10c between the projections (FIG. 8c). Projections 10f are able to bend away from slot 10 so as to allow pin 7 to pass therethrough and enter 10c, but they cannot bend toward slot 10 so as to allow pin 7 to exit 10c. If desired, one or more teeth 200 may be positioned in notch 10c between the opening to notch 10c and projections 10f, although they are not required for proper functioning of the retractable syringe. Teeth 200, if present, are designed so that the pin may be reversibly pushed into notch 10c through the deliberate application of a force having at least a first defined magnitude. The projections 10f are preferably designed so that force of the first defined magnitude $F_1$ is insufficient to force pin 7 through projections 10f. Force of a second defined magnitude $F_2$, greater than the first defined magnitude, is required to force pin 7 through projections 10f. Thus, the pin may be reversibly locked into notch 10c by pushing it into notch 10c with a force F, where $F_1 \leq F < F_2$; and the pin may be irreversibly locked into notch 10c by pushing it into notch 10c with a force of $F_2$ or greater. It is possible to omit notch 10b from the container structure entirely, and use notch 10c for both reversibly and irreversibly locking pin 7 into position. This is, however, much preferred to use notches 10b and 10c as separate locking mechanisms, due to the possibility of unintentionally irreversibly locking pin 7 into notch 10c when attempting to use notch 10c as a reversible lock.

A second version of the mechanism for irreversibly engaging the pin at the second defined location in said longitudinal slot so as to hold said needle assembly in a position where the needle is retracted within the container is provided. This version of the mechanism features the rigid ring 9a mounted on wall 9 of the container; and a rigid tongue 9b attached to one end of the rigid ring by a living hinge 9c (FIG. 9a). This tongue is positioned so that it extends from the end of the container with syringe barrel-receiving opening 13. The second end of the rigid ring is substantially flush with one side of the slot 10b, without blocking slot 10b (slot 10c is not present in this embodiment). To permanently lock the needle assembly in a retracted position, pin 7 is moved into slot 10b, exactly as for the procedure for reversibly locking pin 7 into position. The rigid tongue is folded in the direction of arrow A against the external surface of the ring and irreversibly secured against the external surface of the ring so that the end of the rigid tongue blocks the opening of slot 10b while pin 7 is inside slot 10b. To accomplish this, the tongue is preferably designed so that it is colinear with slot 10 when it is in its initial, unfolded state, and has a length which is at least equal to the sum of the longitudinal length of the rigid ring and the width of slot 10b. To secure the tongue against the external surface of the ring, a hook 9d on the rigid tongue irreversibly snaps around the second end of the rigid ring (FIG. 9b). Hook 9d also blocks the opening to slot 10b. Alternatively, a post 9e on the rigid tongue may irreversibly snap into a hole 9f in the external surface of the rigid ring (FIG. 10). A projection on the end of the rigid tongue fits into slot 10, blocking the opening to slot 10b.

One difficulty in manufacturing an article of this type lies in the difficulty in getting the pin on the needle assembly to properly engage slot 10. For example, the invention of D'Amico (vide supra) presents a substantially cylindrical hub having a radially protruding pin attached thereto positioned within a tubular container. The inner circumference of the container is substantially the same as the outer circumference of the hub. The pin is positioned within a slot in the wall of the container, where each end of the slot is closed. However, this article is difficult to manufacture inexpensively. When the hub slides into the container, the radially protruding pin is blocked by the end of the tubular container wall, and cannot readily enter the container.

This invention attempts to solve this problem. When the container is manufactured in one piece with a slot 10 which is closed at both ends, the combination of pin 7 and crosspiece 8 will not pass through slot 10 when the needle assembly of FIG. 1a is positioned inside the container of FIG. 2. To overcome this difficulty, one can position the needle assembly inside the container prior to attaching pin 7, and then insert pin 7 through slot 10 and secure the pin to sleeve 3. Alternatively, the container may be manufactured in two pieces, a tubular container and rigid ring 9a.

Figure 11:
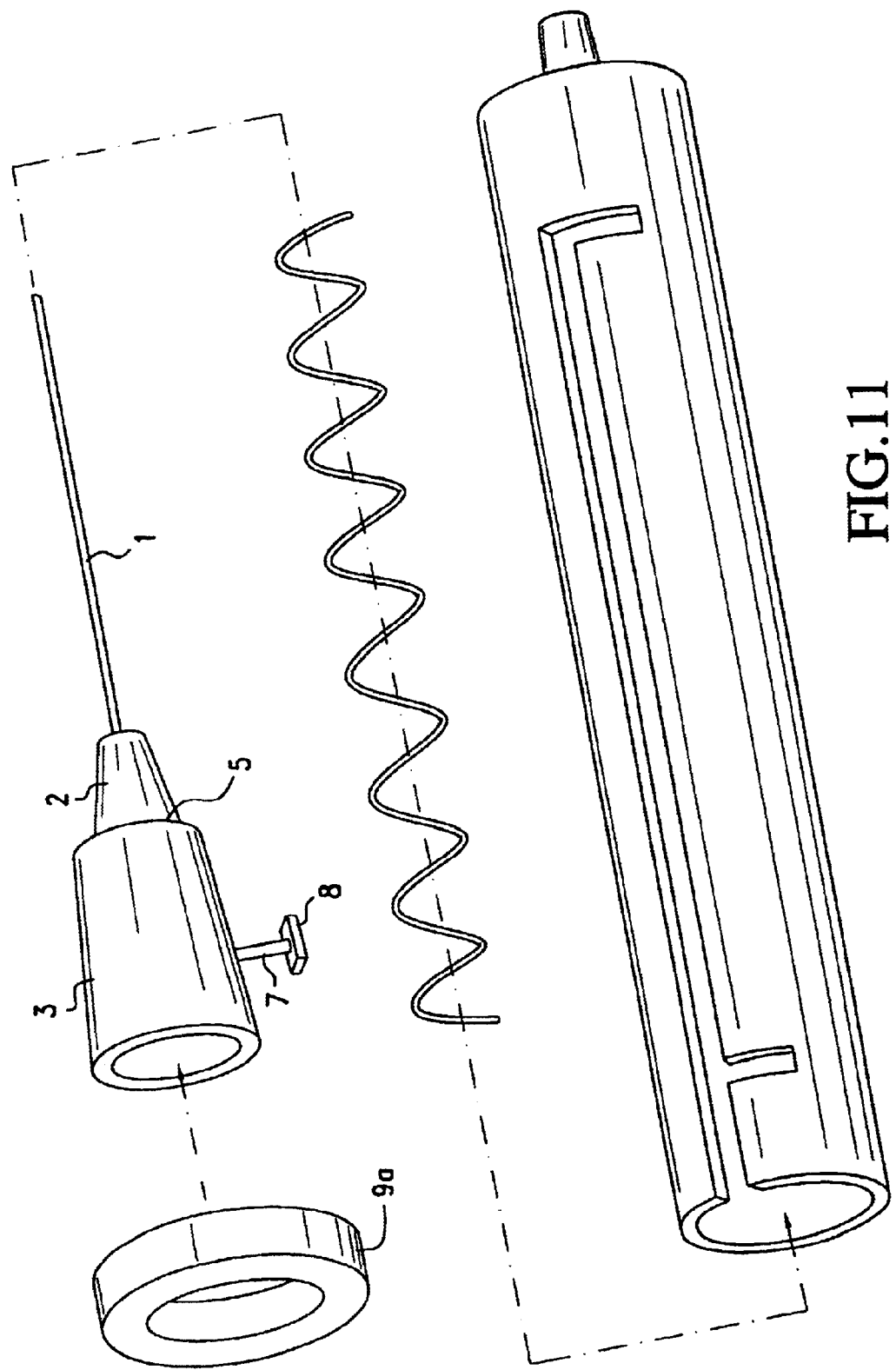
FIG. 11 is an exploded view of the syringe of the current invention, showing how the pieces are assembled.

The retractable syringe needle of the current invention may be made by obtaining a needle assembly as previously described, and obtaining the previously-described container having a tubular wall 9 with an open-ended longitudinal slot 10 therein (FIG. 11). A spring or other biasing means is then inserted into the container. The needle assembly is then inserted into the syringe barrel-receiving end of the container so that pin 7 enters the open end of slot 10, and is slidably engaged by the longitudinal slot. The biasing means engages the hub of the needle assembly and reversibly biases the needle assembly toward a first position where the needle is concealed within the container. The rigid ring is then mounted on the container so that the ring closes the open end of slot 10, preventing the pin 7 from exiting slot 10.

Figure 12:
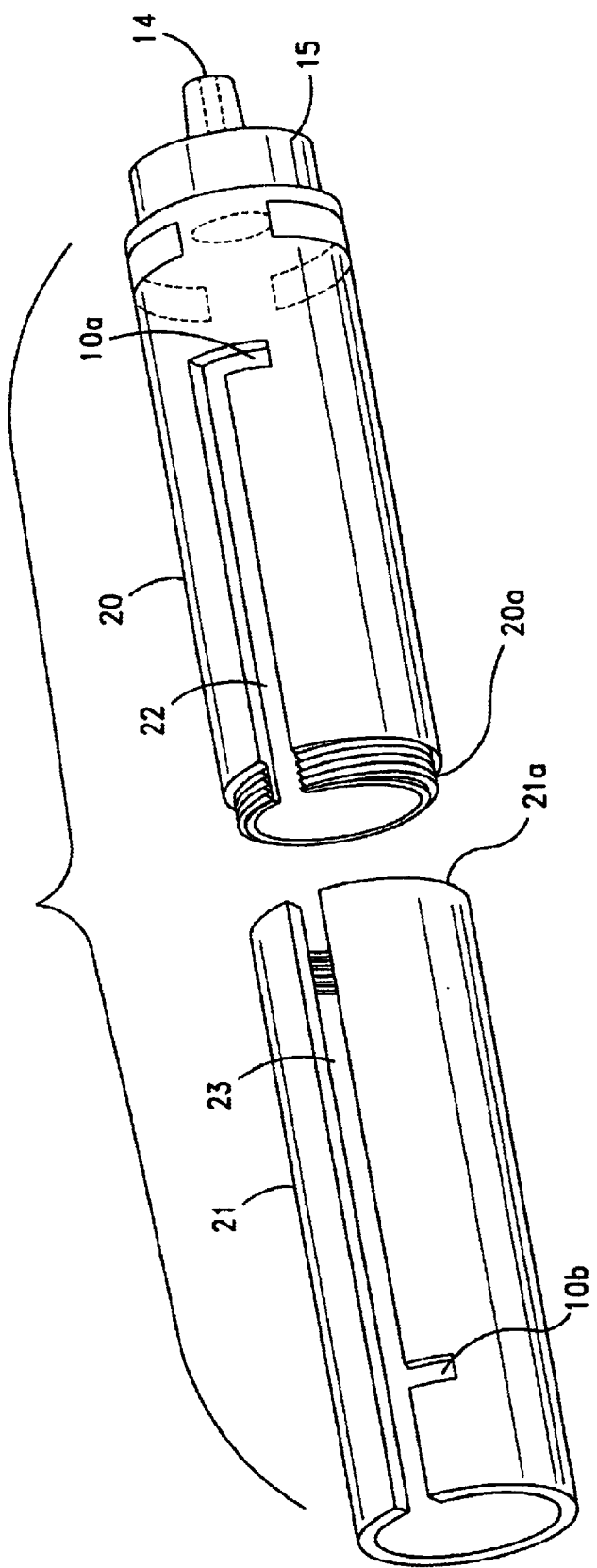
FIG. 12 illustrates the parts used to form an alternate version of the container of FIG. 2.

A second, and less preferred, method of solving the problem involves formation of the container in two parts, as shown in FIG. 12. The container is formed from an anterior portion 20 and a posterior portion 21. Anterior portion 20 has a first open end adapted to receive a syringe barrel and a second open end adapted to receive a hypodermic needle. Ridge 15 is positioned on the interior surface of the wall of anterior container portion 20. A first longitudinal slot 22 runs from the first end of the anterior portion of the container to point 12, near the second end of the anterior portion of the container. Slot 10a meets slot 22 at a right angle. Posterior portion 21 of the container has a first open end adapted to receive a syringe barrel and a second open end adapted to receive a syringe barrel. A second longitudinal slot 23 runs from the first end of the posterior portion of the container to point 11, near the second end of the posterior portion of the container. The first end of 20 and the first end of 21 are adapted to be joined together to form the complete container, by attaching 20 and 21 together so that slots 22 and 23 cooperate to form slot 10.

The manner in which 20 and 21 are joined together is not particularly limited. Parts 20 and 21 may be bonded together by means of a biocompatible adhesive. Alternatively, threaded ends on 20 and 21 may be screwed together, and then secured with a suitable adhesive. Also, a ridge on an interior surface of one piece may snap into a groove on an exterior surface of another piece. The ridge may be treated with an adhesive prior to snapping it into the groove. Finally, if 20 and 21 are made from a thermoplastic material (i.e., polyolefin), they may be heat-sealed together. In the embodiment illustrated in FIG. 12, a threaded end 20a on container portion 20 is screwed onto a threaded end 21a on container portion 21.

Figure 13:
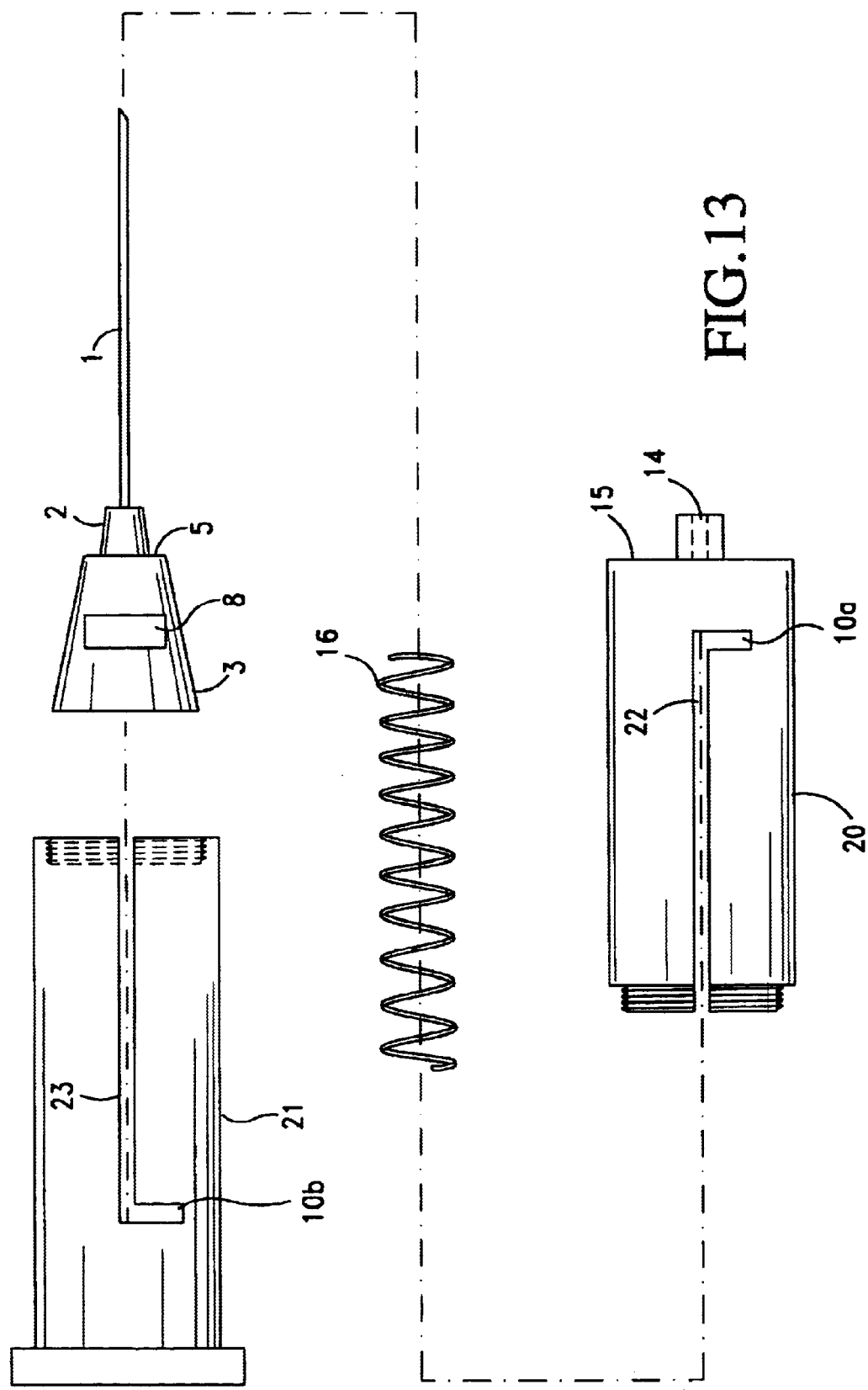
FIG. 13 is an exploded view of the retractable hypodermic safety needle within a container shown in FIG. 12.

The complete assembly is manufactured in the following manner, shown in FIG. 13. A spring 16 and the needle assembly are joined together by joining a first end of the spring to ridge 5 on hub 2. The needle 1 is positioned along the helical axis of the spring. This assembly is then positioned within the anterior portion 20 of the container so that a second end of the spring engages ridge 15. Container portion 20 is then joined to container portion 21 so that:

a) slots 22 and 23 line up to form slot 10; and
b) pin 7 is slidably engaged by slot 10.

Alternatively, hub 2 may be positioned within posterior portion 21 so that pin 7 engages slot 23, and then part 20 may be joined to part 21 container so that the second end of the spring engages ridge 15. Again, when joining pieces 20 and 21, care should be taken to ensure that slots 22 and 23 are aligned so as to form a single slot 10 which engages pin 7.

This assembly method allows the safety needle to be assembled quickly and easily, and avoids the difficulty of trying to position the needle inside a fully assembled container without damaging the pin by forcing it past the rim of the container.

Figure 14:
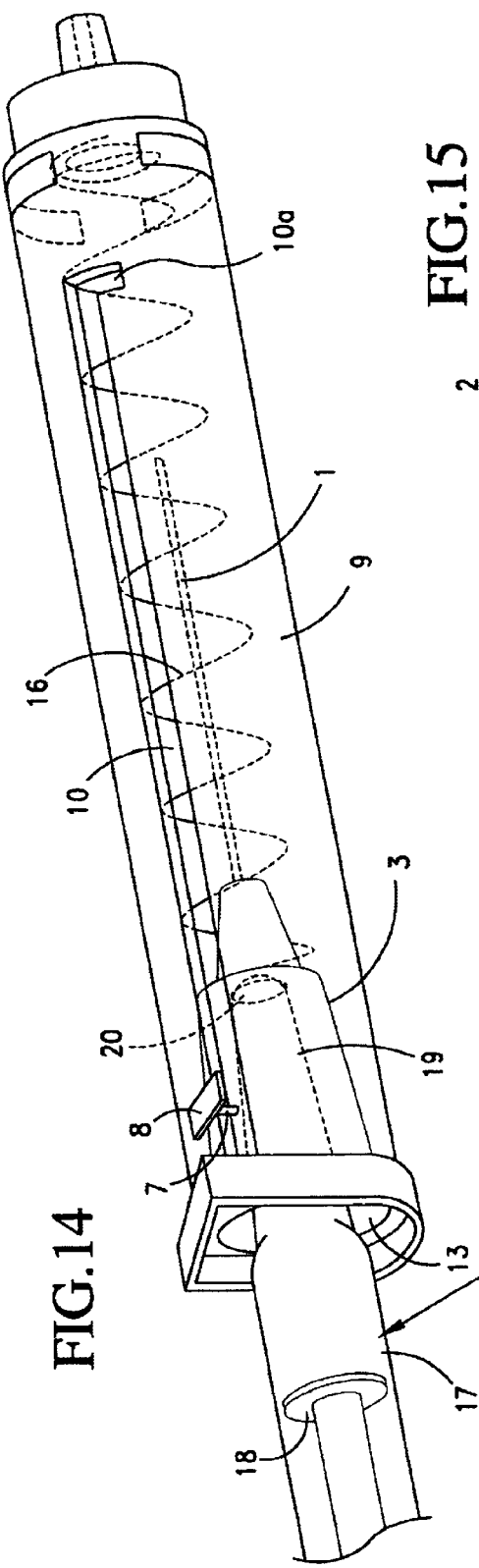
FIGS. 14 and 15 show a modified version of the apparatus of FIG. 4.
Figure 15:
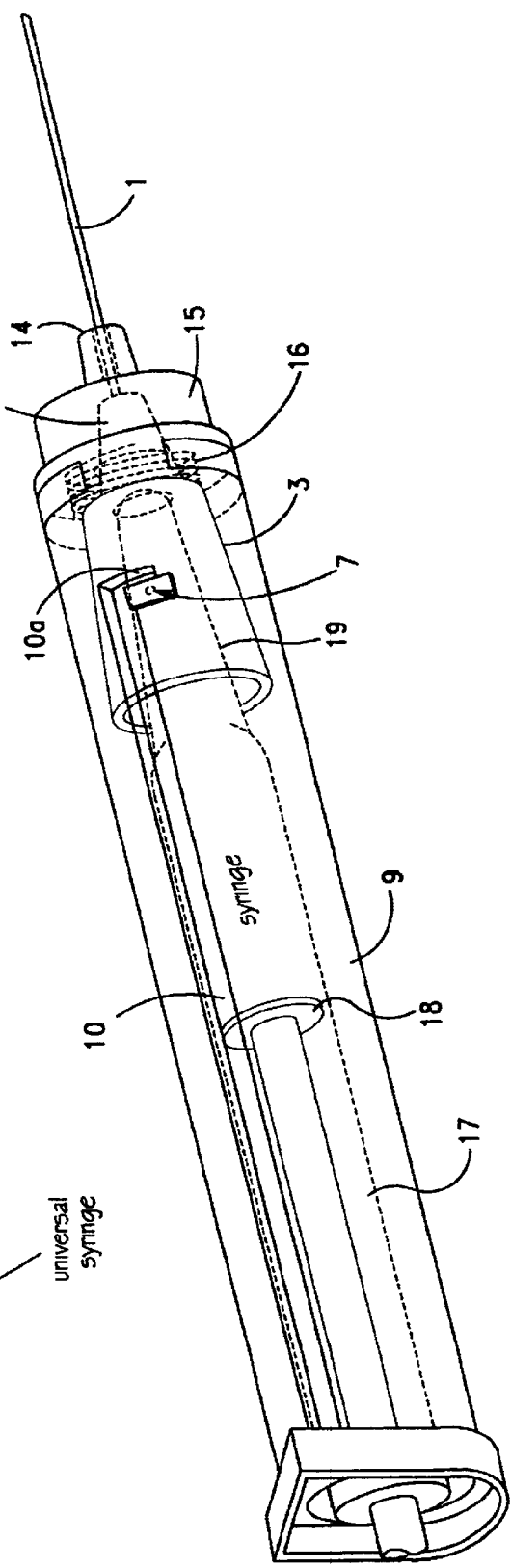

FIGS. 14 and 15 illustrate use of a syringe assembly with the safety needle of FIG. 3. The syringe comprises a syringe barrel 17, and a syringe plunger 18 slidably mounted therein. Barrel 17 has a frusto-conical tip 19 adapted to enter cavity 6 of sleeve 19 (cavity 6 is not shown in FIGS. 5 and 6, as it is occupied by tip 19.). Tip 19, after insertion into cavity 6, frictionally engages the interior of sleeve 3, forming a leakproof seal. A hole in tip 19 receives fluids which have passed through the bore of needle 1.

As shown in FIG. 15, syringe barrel 17 may be used to push the needle assembly within the container toward the second end of the container, compressing the spring and causing needle 1 to emerge through hole 14. In this position, the container encases at least a portion of barrel 17. Barrel 17 may then be rotated, causing sleeve 3 to rotate. This causes pin 7 to enter slot 10a, locking the syringe needle into position. The assembled syringe, with the needle exposed, may then be used to take a sample of a fluid. More particularly, the assembled syringe may be used to administer an injection to a patient, or to take a sample of arterial or venous blood from a patient.

After use, the contaminated needle may be discarded by rotating barrel 17 in the reverse direction to free pin 7 from slot 10a. This allows spring 16 to decompress, causing the container to slide forward off of the syringe barrel and cover needle 1. The syringe barrel may then be separated from sleeve 3, and the container with the needle concealed therein may be discarded with minimal risk of injury from contact with the contaminated needle. The syringe barrel and plunger may be discarded, or sterilized in an autoclave for reuse.

As shown in FIG. 16, it is possible to secure two pins 7, each having a crosspiece 8 mounted thereto, on a single needle assembly, where the two pins are directed in opposite directions. Such a needle assembly may be mounted in a container having two slots 10a in opposite sides of wall 9. A transverse slot 10a intersects each slot 10, with each slot 10a running in the same direction (i.e., either clockwise or counterclockwise, when viewed from the second end of the container along the container axis). This version of the apparatus operates in the same manner as the assembled apparatus of FIG. 3. The only difference is that the presence of the second pin anchors hub 2 of the needle assembly more firmly along the axis of the container (FIG. 17).

FIG. 18 shows an alternative embodiment of the needle assembly of FIG. 1a. This embodiment of the needle assembly features a hollow straight needle 29 having two ends. The needle 29 extends through a hub 30, so that a first end of the needle 29a points in a forward direction, and a second end of the needle 29b points in a reverse direction. Pin 7 is rigidly connected with said hub, and extends in a radial direction. Crosspiece 8 is connected with the pin at a defined distance from the hub. Preferably, a rubber sheath 31 covers end 29b of needle 1.

Figure 19:
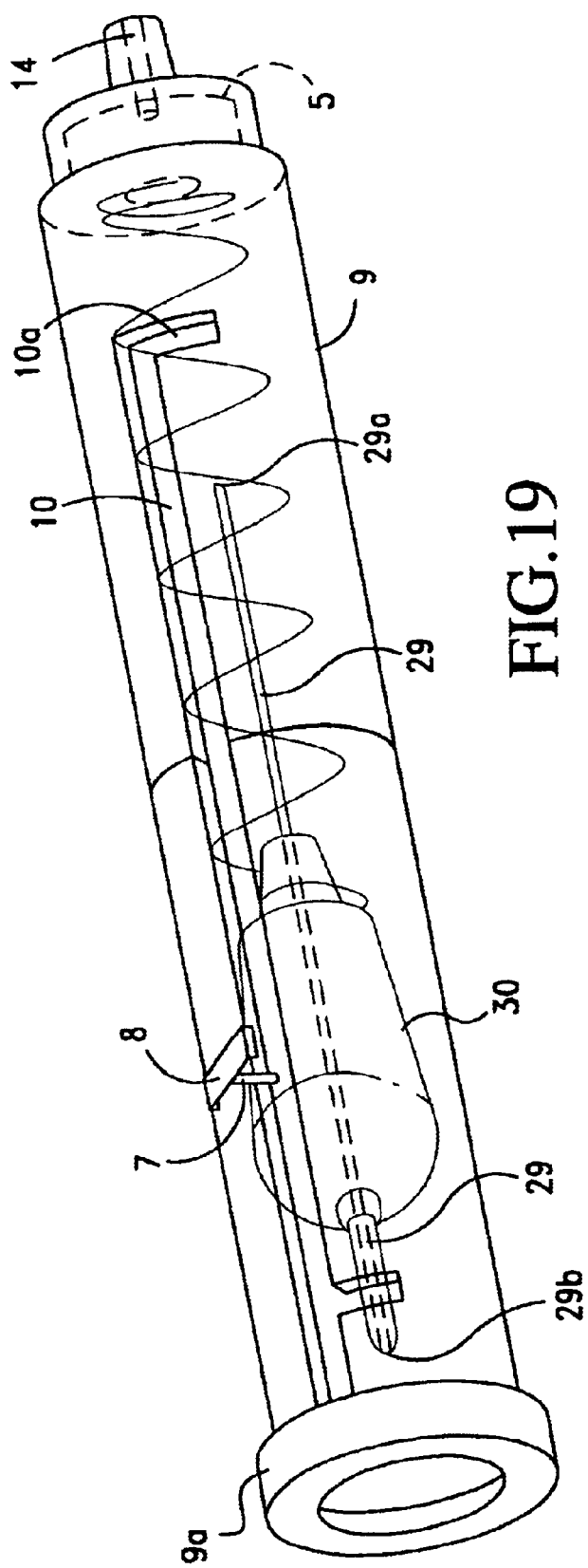
FIG. 19 shows an apparatus for taking blood samples, using the needle assembly of FIG. 18.

FIG. 19 shows the needle assembly of FIG. 18 mounted within a container similar to that of FIG. 2. The container features a defined cylindrical axis and has a tubular wall 9 with a longitudinal slot 10 therein. A first open end of the container is adapted to receive a receptacle for venous blood, preferably an evacuated test tube with a rubber stopper, and a second open end adapted to allow the first end of the hollow needle to pass therethrough. The longitudinal slot extends from the first open end of the container to a defined point near the second open end of the container, where the longitudinal slot is open-ended at the first open end of the container and closed at the second open end of the container. A rigid ring is positioned over the first open end of the container so as to close the open end of the longitudinal slot. A plurality of circumferential strengthening ridges may be positioned on the exterior surface of the container. The needle assembly is mounted within the container so that (i) the first end of the needle, 29a, is directed toward the second open end of the container, and (ii) pin 7 on the needle assembly is slidably engaged by longitudinal slot 10, with crosspiece 8 acting to support hub 30 so that it is positioned on the axis of the container. End 29a of needle 29 is exposed by using the thumb or finger to manually slide piece 8 forward toward needle-receiving opening 14, carrying hub 30 toward the second end of the container until the needle end 29a passes through opening 14 and is exposed. Piece 8 is then pushed sideways until pin 7 enters slot 10a, locking the needle into the exposed position. The needle may then be inserted into a patient's blood vessel. The rubber sheath prevents the patient's blood from traveling through the needle. Positioned inside the container, there is a spring or other means for biasing the needle assembly towards a position where the needle is concealed inside the container; the biasing means acts to prevent premature exposure of the needle.

The double-ended safety needle additionally features a first notch 10a which intersects the longitudinal slot at a first defined location near the needle-receiving opening 14 in the container. The needle may be reversibly secured in an exposed position by pushing pin 7 toward opening 14 until pin 7 is positioned adjacent to notch 10a, and then pushing pin 10b sideways into notch 10a. The biasing means presses the pin against the rear wall of notch 10a, securing the needle assembly into position. Similarly, the needle may be reversibly secured in a concealed position by pushing pin 7 toward opening 13 until pin 7 is positioned adjacent to a second notch 10b near opening 13 in the container, and then pushing pin 10b sideways into notch 10b. As previously described, each of notches 10a and 10b may be straight transverse notches, or notches 10a and 10b may each independently be a T-shaped notch (as seen in FIG. 6a), a L-shaped notch (FIG. 6b), or a C-shaped notch (FIG. 6c). Also, each notch may be provided with teeth 200 which are spaced sufficiently closely together that the pin may not be pushed into, or out of, the notch without the deliberate application of force.

Figure 8A:
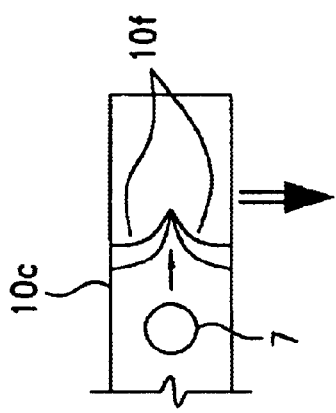
Figure 8B:
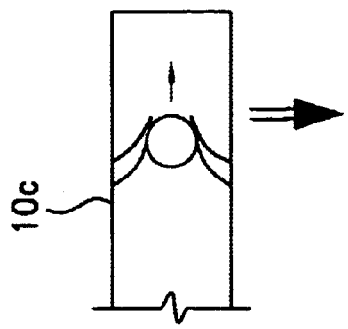
Figure 8C:
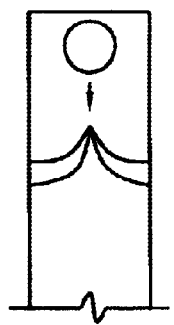

A means for irreversibly engaging the needle assembly in a retracted position comprises a third notch 10c, where notches 10b and 10c are colinear and extend in opposite directions from the longitudinal slot as seen in FIGS. 7 and 8. A pair of flexible projections having tips which contact each other extend from opposite sides of notch 10c. The tips are adapted to allow the pin engaged by the slot to pass therethrough when the pin enters notch 10c from the longitudinal slot, and to not allow the pin to pass therethrough to exit notch 10c.

Alternatively, the means for irreversibly engaging the pin may comprise a rigid tongue attached to one end of the rigid ring by a living hinge, as seen in FIGS. 9 and 10. The rigid ring is positioned so that the other end of the rigid ring is substantially flush with one side of notch 10b (no notch 10c is present in this embodiment). To secure the pin in notch 10b, the rigid tongue is folded against an external surface of the ring and irreversibly secured against the external surface of the ring so that the end of the rigid tongue blocks the opening of the second notch.

To hold the rigid ring in position relative to the wall of the container, a circumferential ridge 9g on the interior surface of the rigid ring 9a snaps into a circumferential groove 9h on the exterior surface of the container (FIG. 20). Also, a ridge 9i on the interior of the rigid ring may fit into the open end of slot 10 to prevent rotation of the ring relative to the slot.

Figure 21:
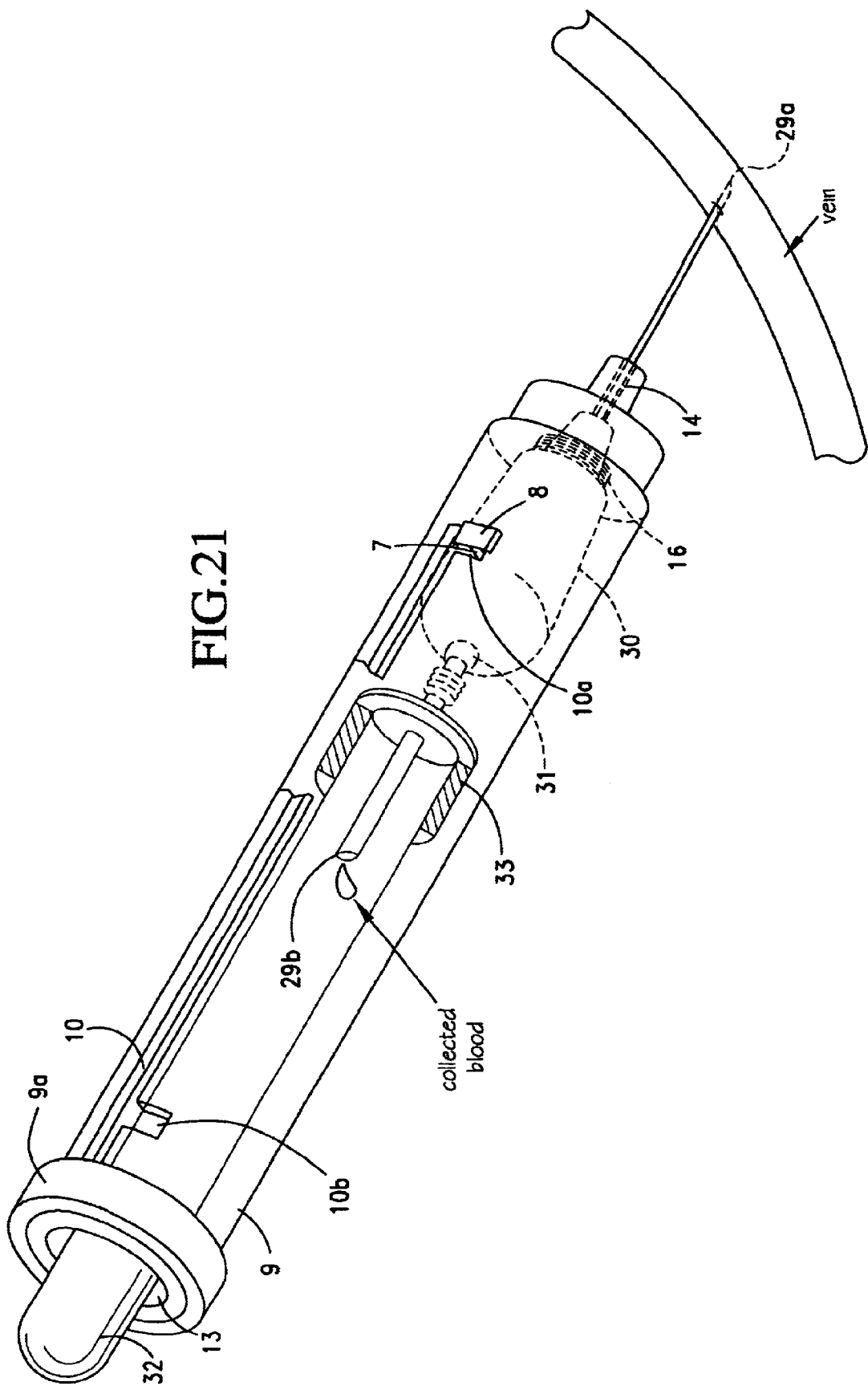
FIG. 21 shows the apparatus of FIG. 19 in use.

The assembly of FIG. 19 may be used with a receptacle for receiving a blood sample, as shown in FIG. 21. This receptacle is a test tube 32 having an open end. A rubber septum 33 seals the open end of the test tube. The interior of the test tube may be under vacuum. While needle 29 is in the patient's blood vessel, the end of the test tube which is sealed by septum 33 is inserted into opening 13 of the container until septum 33 contacts rubber sheath 31. The test tube is then pushed toward hub 30, and septum 33 pushes the end of rubber sheath 31 along needle 29 toward hub 30, exposing end 29b of needle 29. End 29b of needle 29 pierces the rubber sheath 31 and septum 33, entering the test tube. Blood from the patient then travels through hollow needle 29 into the test tube. After taking a sample of the patient's blood, test tube 32 is removed from the container. Rubber sheath 31 resumes its original configuration, covering end 29b of the needle and cutting off the flow of blood. Needle 29 is then withdrawn from the patient's blood vessel. Crosspiece 8 is then pushed sideways until pin 7 exits slot 10a, unlocking the needle. Spring 16 then causes needle 1 to withdraw into the container.

As in the syringe needle assembly of FIG. 3, piece 8 is sufficiently large that it cannot pass through slot 10 into the interior of the container, and is rigidly secured to a defined position along the length of pin 7, where the defined position on pin 7 is chosen so that hub 30 of the needle assembly is positioned along the cylindrical axis of the container. More particularly, the distance between the axis of hypodermic needle 1 and crosspiece 8 is equal to the one half the external diameter of the wall 9 of the container. This retains needle 29 along the axis of the container.

The use of crosspiece 8 to retain needle 1 in position is particularly important in an apparatus for obtaining blood samples. The container has to be wide enough to receive the test tube, which in turn is normally wider than hub 2. Without crosspiece 8, pin 7 would slip out of slot 10, and end 29b of needle 29 would fall against the inner surface of wall 9. Needle 29b would then be incorrectly positioned to penetrate septum 33.

A threaded male joint 34 may surround opening 13 at the first end of the container of FIG. 2, and a threaded male joint 35 may surround opening 14 at the second end of the container. Cap 36 having a threaded female joint may be screwed onto joint 34, covering opening 13, and cap 37 having a threaded female joint may be screwed onto joint 35, covering opening 14. This is normally done whenever the needle is not intended to be exposed, so as to minimize the risk of accidental contact with the tip of the needle.

Figure 22:
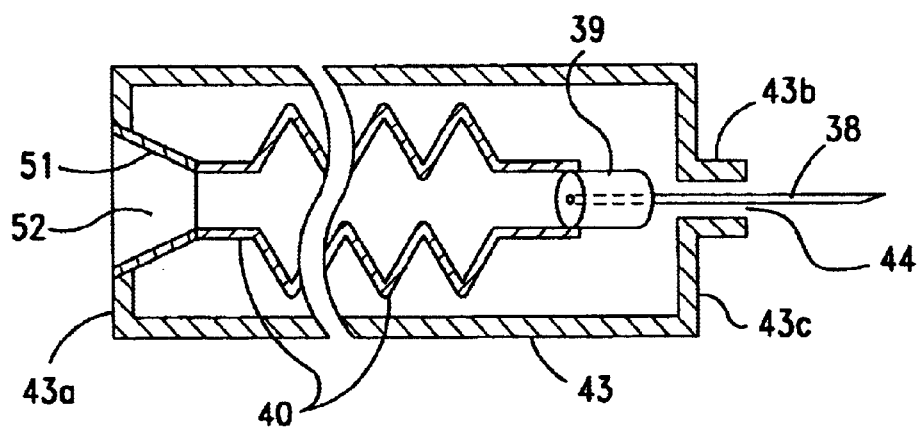

A further embodiment of the invention will now be discussed. This second embodiment, shown in FIG. 22, features a hollow hypodermic needle 38 and a cylindrical hub 39 having an axial passage therethrough. The hollow needle is rigidly connected with the hub so that the axial passage and the interior of the hollow needle form a continuous conduit. Hub 39 is secured to one end of an adjustable-length tube 40 so that the interior of hollow needle 38 makes fluid contact with the interior of tube 40. The tip of a syringe barrel, which may be cylindrical or frusto-conical, may be frictionally secured to the other end of the adjustable-length tube so that the interior of the syringe barrel is in fluid communication with the interior of the adjustable-length tube. Tube 40 is preferably impermeable to liquids, non-elastic, and axially collapsible. By collapsing the tube in an axial direction, the length of tube 40 may be changed from a first extended length to a second contracted length. The tube may then be extended in an axial direction, restoring the length of the tube to the first extended length.

A tubular sheath 43 is disposed around the adjustable-length tube 40. The tubular sheath 43 has a first end 43a which is rigidly connected with the first end of the adjustable-length tube and a second end 43b having an opening 44 which is sufficiently large to allow the end of the hypodermic needle 38 to pass therethrough. The outer surface of member 51 is rigidly secured to end 43a of sheath 43. When the apparatus is not in use, the opening at each end of the tubular sheath may be covered by a cap (not shown in the drawings). The caps may screw onto the sheath, or snap onto the sheath.

The retractable needle featuring the adjustable-length tube additionally features a means to alter the length of the adjustable-length tube from the contracted length to the extended length. This length-altering means includes a longitudinal slot running along the length of the tubular sheath; and a knob or pin 7 connected to the hub of the needle assembly. The knob or pin slidably engages the longitudinal slot, and may be used to change the length of the adjustable-length tube from its collapsed state to its extended state. The retractable needle additionally features a means for reversibly securing the knob at a first position along the length of the longitudinal slot, where the tube is contracted when the knob is in said first position; a means for reversibly securing the knob at a second position along the length of the longitudinal slot, where the tube is extended when the knob is in said first position; and a means for irreversibly securing the knob at said first position along the length of the longitudinal slot.

The structures of the reversible and irreversible securing means are substantially as previously described.

Figure 23A:
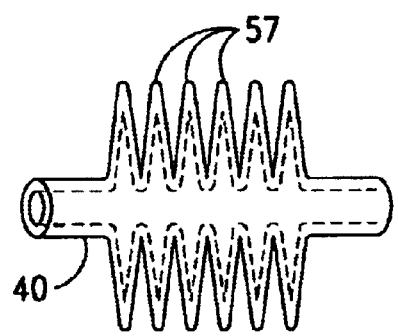
FIGS. 23a, 23b, 24a, and 24b show different embodiments of the adjustable-length tube.
Figure 23B:
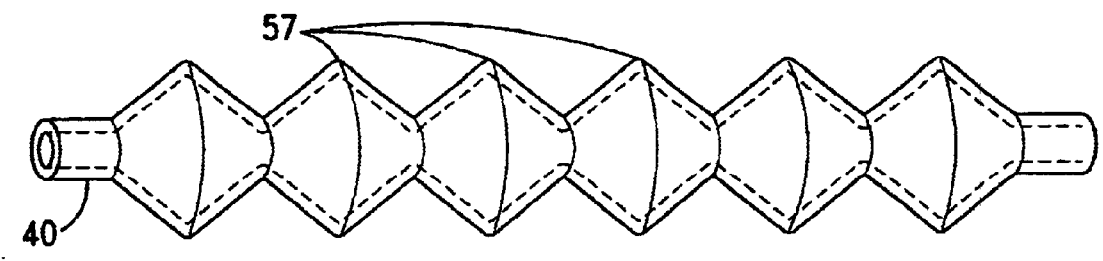

The preferred embodiments of the adjustable-length tube 40 will now be discussed. The most preferred type of adjustable-length tube 40 contemplated for use in this invention features a series of circumferential pleats 57 disposed along the length of the tube, as shown in FIGS. 23a and 23b. When tube 40 is in its contracted or collapsed state (FIG. 23a), pleats 57 are folded together. The adjustable-length tube may be lengthened by pulling one end of tube 40 (the end to which the hub is attached) away from the other, causing pleats 57 to unfold (FIG. 23b).

Figure 24A:
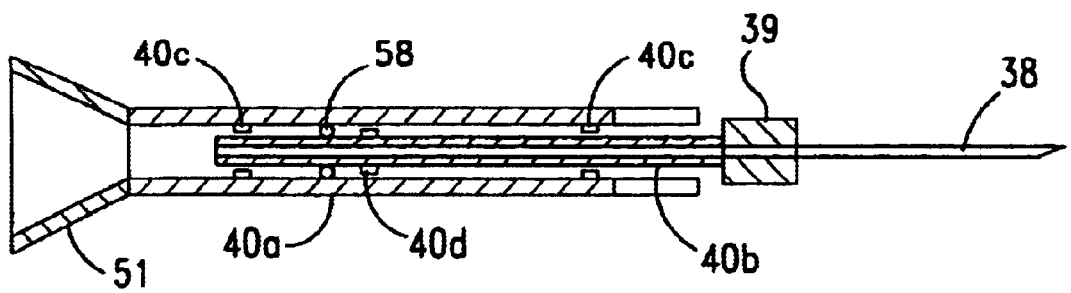
Figure 24B:
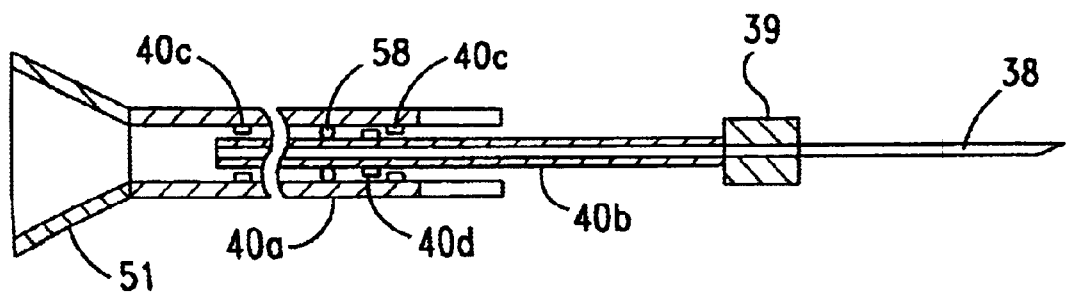

Another embodiment of adjustable-length tube 40 is a telescoping tube made from an outer tube 40a and an inner tube 40b, as shown in FIGS. 24a and 24b. The inner tube is slidably disposed within the outer tube. A first end of outer tube 40a is adapted to be secured to syringe barrel 40 through conical member 51, as previously described. A first end of inner tube 40b is adapted to be secured to hub 39. The inner tube 40b may be moved from a position where tube 40b is entirely or primarily disposed within tube 40a (FIG. 24a), contracting tube 40, to a position where tube 40b is mostly exposed (FIG. 24b), expanding tube 40. Ridges 40c on the interior of outer tube 40a interact with a ridge 40d on the outer surface of tube 40b, acting as stops to prevent removal of tube 40b from tube 40a. Preferably, a leakproof sealing material 58 is disposed between the outer surface of the inner tube and the inner surface of the outer tube. This sealing material may be a hydrophobic, biocompatable polymer with a low coefficient of friction, such as silicone or teflon.

When the adjustable-length tube is contracted, the hypodermic needle is entirely disposed within the sheath (FIG. 25a). When the adjustable-length tube is extended, the end of the hypodermic needle is exposed through opening 44 in the second end of the sheath (FIG. 25b). If desired, the interior diameter of the sheath 43 may narrow from a diameter which is great enough to receive the adjustable-length tube 40 to a diameter which is little greater than the diameter of needle 1. This narrowing occurs at a point 43c near the opening 44. When the needle is disposed within the sheath, the pointed end of the needle then occupies a position where the inner diameter of the container is small (FIG. 19a). This helps prevent the needle point from moving away from the axis of the container. If desired, a spring or other biasing means may bias the hub away from opening 44. This causes the adjustable-length tube to preferentially occupy its contracted state, with the needle being retracted within the container.

Figure 26:
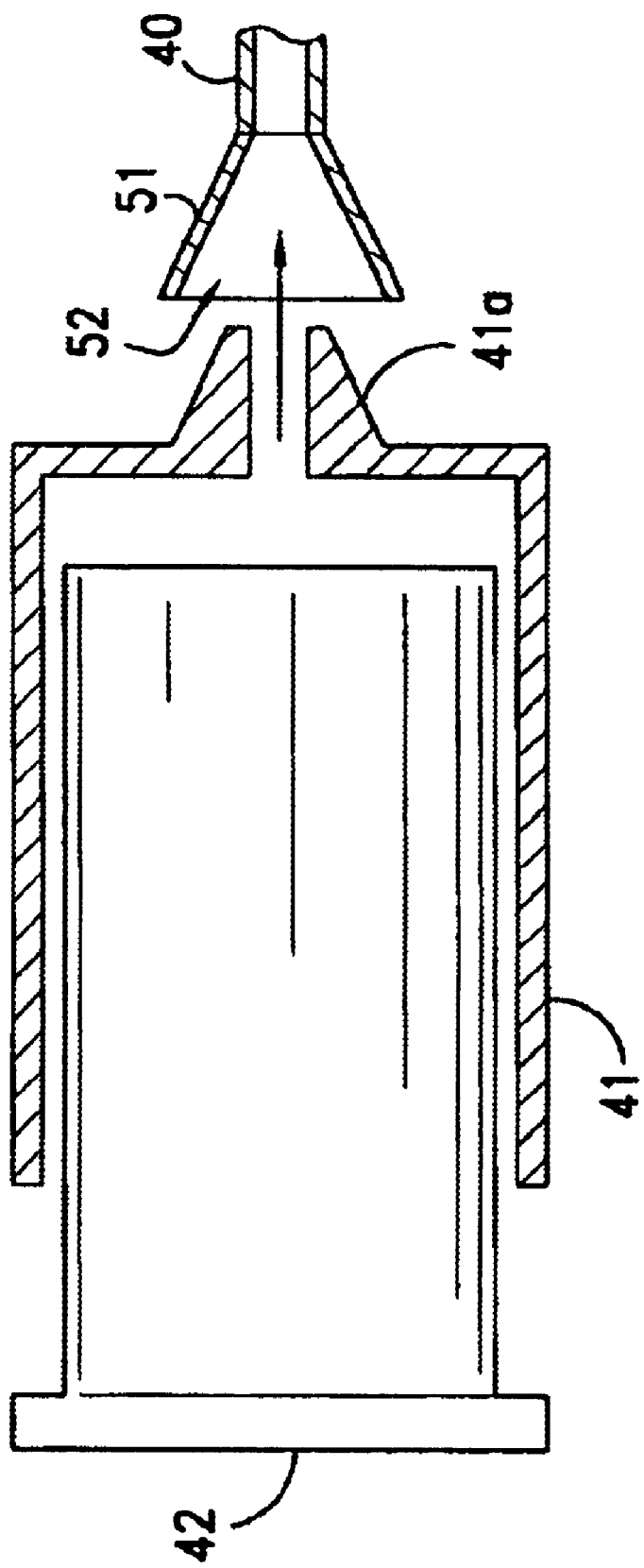
FIG. 26 shows the apparatus of FIG. 22 in use.

This embodiment of the invention may be used to withdraw fluid samples from a patient's bloodstream, or to inject medicinal fluids into a patient's bloodstream. A syringe barrel 41 having a plunger 42 slidably mounted therein may be reversibly secured to the other end of the adjustable-length tube 40 so that the interior of the syringe barrel is in fluid contact with the interior of the adjustable-length tube, as shown in FIG. 26. By raising the plunger and creating a partial vacuum within barrel 41, fluids may then be drawn through needle 38 (not shown in FIG. 26) and tube 40 into barrel 41. The syringe barrel 41 is secured to the first end of the adjustable-length tube 40 by means of a hollow conical member 51. The inner surface of member 51 defines a cylindrical or frustoconical cavity 52 adapted to frictionally engage the tip 41a of the syringe barrel. The conical member 51 has a passage 51a therethrough. Member 51 is connected to the end of the adjustable-length tube 40 to which hub 39 is not secured. The cavity 52 makes fluid contact with the interior of the adjustable-length tube 40 through the passage 51a. As the outer surface of member 51 is rigidly secured to the first end of the tubular sheath 43 (sheath 43 is not shown in FIG. 21), sheath 43 is immobile relative to a syringe barrel 41 connected to tube 40.

Figure 27:
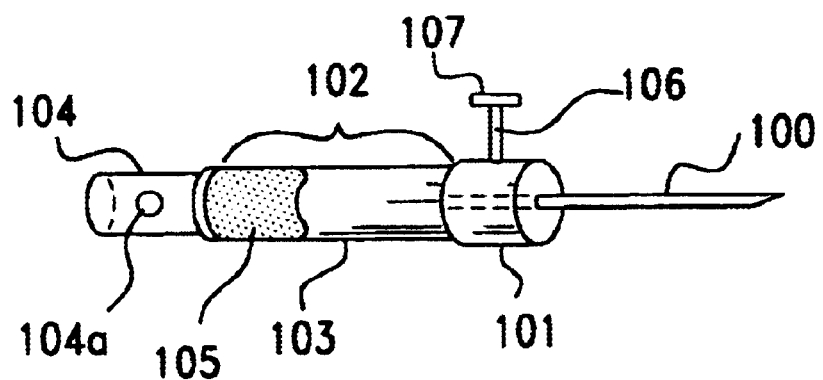
FIG. 27 shows a needle assembly for use with a catheter.
Figure 28:
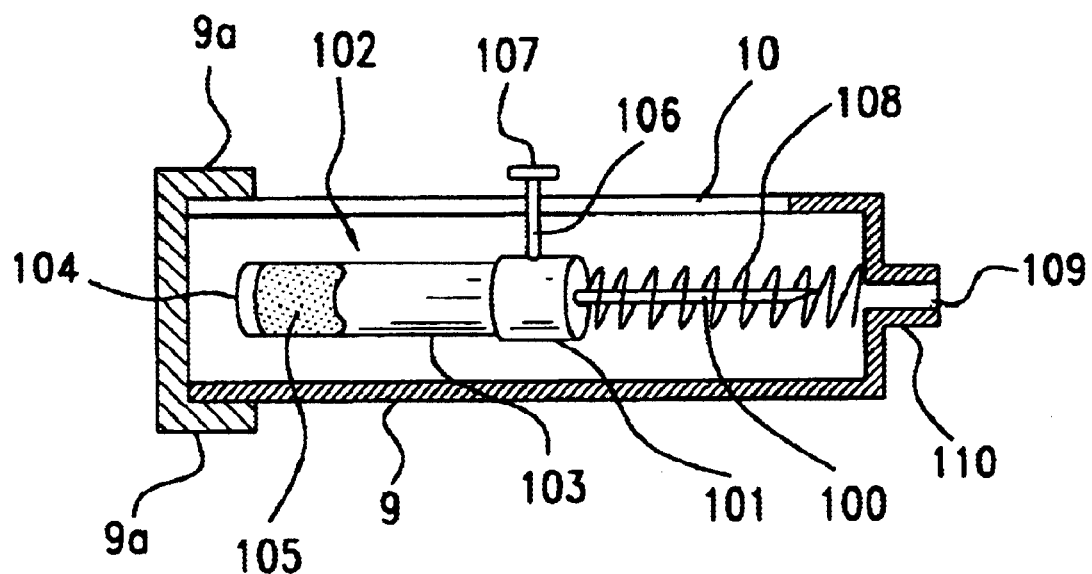
FIG. 28 shows a retractable needle for use with a catheter.

A needle assembly for use with a catheter is assembled as shown in FIG. 27. Hollow needle 100 extends from one end of a cylindrical hub 101, and penetrates the second end of the hub. A flash chamber 102 features a tubular side wall 103 having a first end which makes a watertight seal with the second end of hub 101. Cap 104 closes the second end of tubular wall 103, making a second leakproof seal. The interior of flash chamber 102 is in fluid communication with the interior of hollow needle 100, so that fluid may travel through the needle 100 into chamber 102. The tubular wall of chamber 102 is normally transparent or translucent, so that blood entering the flash chamber through needle 100 is readily visible. A small plug of absorbent material 105, such as cotton, is normally present in flash chamber 102, just under cap 104, although this is not an essential feature of the invention. A stem 106 protrudes radially from hub 101. A thumbrest 107 is attached to stem 106. The needle assembly having the flash chamber is positioned inside a container with a defined cylindrical axis having a tubular wall 9 with a longitudinal slot 10 therein. The container has a first end having an opening 109 adapted to allow the hollow needle to pass therethrough and a closed second end. A tubular extension 110 of the container surrounds opening 109. The pin of the needle assembly is slidably engaged by the longitudinal slot in the container, so that said needle assembly may be moved from a first position where the needle is within the container to a second position where the needle is exposed by sliding the pin toward the first end of the container. A spring 108 reversibly biases the needle into the first position. A notch 10a may be used to reversibly retain the needle in an exposed position, while a notch 10b may be used to reversibly retain the needle in a retracted position, exactly as previously described. A means for irreversibly retaining the needle in its retracted position may comprises a third notch 10c, where notches 10b and 10c are collinear and extend in opposite directions from the longitudinal slot. A pair of flexible projections having tips which contact each other extend from opposite sides of the third notch, directed away from slot 10. The projections allow the pin engaged by slot 10 to pass therethrough when the pin enters notch 10c from the longitudinal slot, and to not allow the pin to pass therethrough to exit notch 10c (FIGS. 7 and 8). Alternatively, the container may comprises a housing having a first open end adapted to admit the needle assembly and a second open end adapted to admit the hollow needle, and a cap 9a which closes the first open end of the housing. The longitudinal slot extends from the first open end of the housing to a defined point near the second open end of the container, said longitudinal slot being open-ended at the first open end of the container and closed at the second open end of the container. The cap has a skirt that extends over the exterior of the housing until it reaches the edge of the first notch. A rigid tongue is attached to the cap by a living hinge. After pin 7 is positioned in slot 10b, the rigid tongue may be folded against the skirt of the cap and irreversibly securing against the external surface of the skirt so that the end of the rigid tongue blocks the opening of 10b, preventing pin 7 from exiting notch 10b, exactly as previously described (FIGS. 9 and 10).

Figure 29:
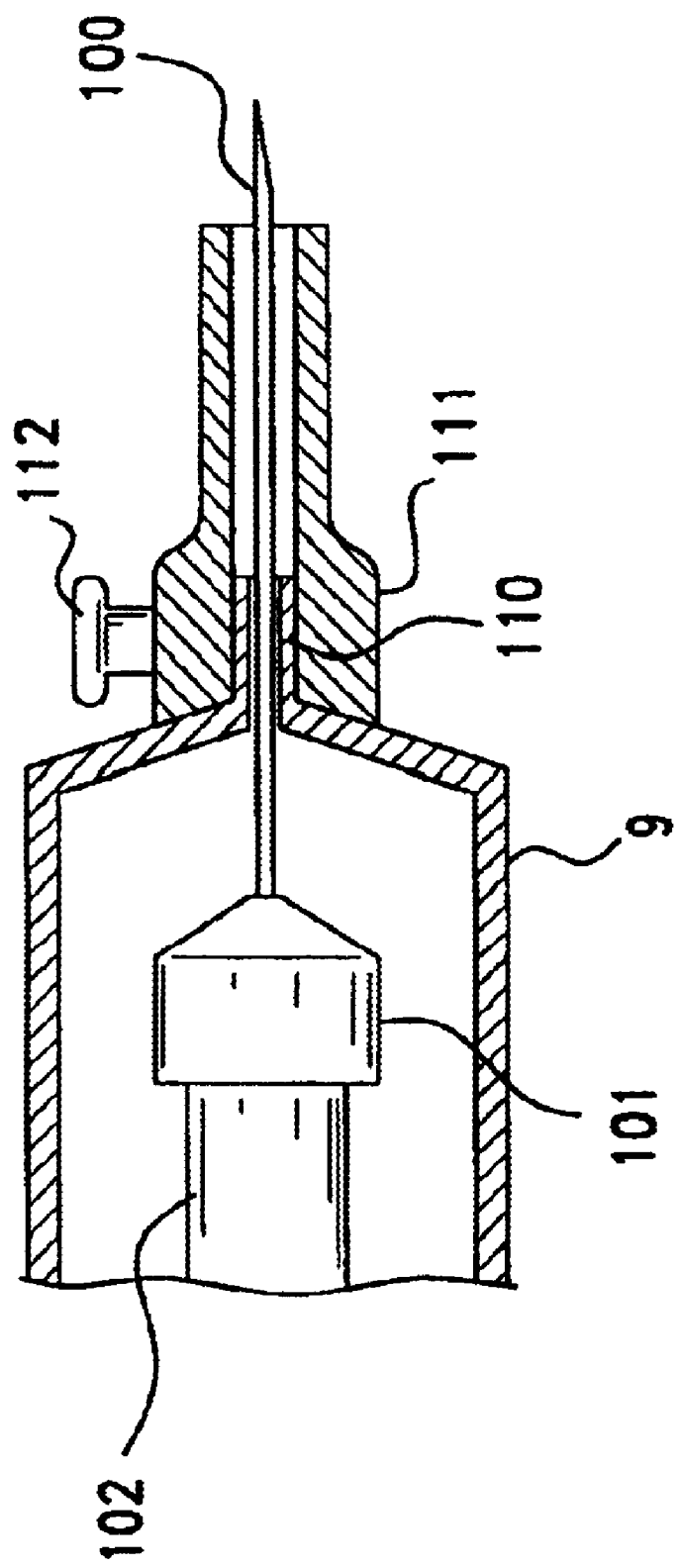
FIG. 29 shows the needle assembly of FIG. 28 with a catheter attached thereto.

When the retractable catheter needle is in its exposed position, a flexible catheter 111 having a longitudinal bore therethrough is supported by the needle 100 (FIG. 29). The tip of the needle is exposed through an opening at one end of the catheter. The other end of the catheter is adapted to fit over extension 110, reversibly securing the catheter in position. A knob or other gripping means 112 allows the user to grasp the catheter after it has been inserted into a patient. The needle may then be withdrawn from the catheter, with the catheter remaining in position in the patient. The needle is then retracted into the container. Normally, the catheter is initially provided in position on the needle, with a protective cap or sheath covering the needle and catheter.

What is claimed is:

1. A retractable syringe needle for use with a syringe, said syringe comprising a plunger and a tubular syringe barrel having a defined outer diameter, said barrel having an open end adapted to receive the plunger and a closed end having a tip projecting therefrom, said tip having a maximum defined diameter which is less than the defined outer diameter of the syringe barrel and a longitudinal bore passing through the tip and the closed end of the barrel, said retractable syringe needle comprising:
   a) a needle assembly featuring:
      a needle-holding mechanism, said needle-holding mechanism comprising a hub and an annular sleeve connected with said hub, said sleeve having an exterior surface and an interior surface, where said interior surface of said sleeve defines a cavity having a diameter which is substantially equal to the maximum defined diameter of the tip of the syringe barrel, the interior surface of the sleeve being adapted to frictionally engage the tip of the syringe barrel;
      a hypodermic needle extending through said hub; and
      a pin directly connected to the exterior surface of said annular sleeve;
   b) a container with a defined cylindrical axis having a tubular wall with a longitudinal slot therein, said container having a first open end adapted to receive a syringe barrel and a second open end adapted to receive a syringe needle, said container having said needle assembly mounted therein so that the pin is slidably engaged by the longitudinal slot, and so that said needle assembly may be moved from a first position where the needle is within the container to a second position where the needle is exposed by sliding the pin toward the second open end of the container and causing the needle to pass through the second open end;
   c) a means for biasing the needle assembly toward said first position; and
   d) a means for releasably engaging the pin at a defined location in said longitudinal slot so as to hold said needle assembly in said second position;
      wherein said means for releasably engaging the pin comprises a notch which intersects said longitudinal slot at said defined location, so that said needle assembly may be releasably held in said second position by sliding said pin out of said longitudinal slot into said notch;
      wherein the hub of said needle-holding mechanism is movably positioned along the defined cylindrical axis of the container, the position of the hub being maintained along the axis by a crosspiece rigidly fixed to a defined location along the length of the pin, said crosspiece being on the exterior of the container, and being unable to pass through the longitudinal slot.

2. The retractable syringe needle of claim 1, wherein the notch is selected from the group consisting of a straight notch which is transverse to the longitudinal slot, a T-shaped slot, a C-shaped slot, and an L-shaped slot.

3. The retractable syringe needle of claim 1, wherein the notch is a T-shaped slot.

4. The retractable syringe needle of claim 1, wherein the notch is a L-shaped slot.

5. The retractable syringe needle of claim 1, wherein the notch is a C-shaped slot.

6. The retractable syringe needle of claim 2, wherein the notch has an opening with two opposing sides; and wherein at least one tooth is provided on each side of the opening to the notch, the teeth being spaced sufficiently closely together that the pin may not be pushed into the notch without the deliberate application of force.

7. The retractable syringe needle of claim 1, wherein the tip of the syringe barrel is cylindrically symmetric, and the interior surface of the sleeve defines a cylindrically symmetric cavity adapted to frictionally engage the tip of the syringe barrel.

8. The retractable syringe needle of claim 1, wherein the interior surface of the sleeve defines a frusto-conical cavity, said sleeve being adapted to frictionally engage a frusto-conical tip of a syringe barrel.

9. The retractable syringe needle of claim 1, wherein the interior surface of the sleeve defines a cylindrical cavity of constant diameter, said sleeve being adapted to frictionally engage a cylindrical tip of a syringe barrel, said cylindrical tip having a constant diameter.

10. The retractable syringe needle of claim 1, wherein the longitudinal slot extends from the first open end of the container to a defined point near the second open end of the container, said longitudinal slot being open-ended at the first open end of the container and closed at the second open end of the container; said syringe needle additionally comprising a rigid ring having a first end and a second end; where the rigid ring is positioned over the first open end of the container so as to close the open end of the longitudinal slot.

11. The retractable syringe needle of claim 10, wherein a series of circumferential ridges are positioned on the exterior of the container, said ridges being effective to strengthen the container.

12. The retractable syringe needle of claim 10, wherein the rigid ring has a circumferential ridge on the interior surface of the ring, and the container has a circumferential groove on the exterior surface of the container near the first open end of the container; and wherein the rigid ring is adapted to fit over the first open end of the container until the circumferential ridge snaps into the circumferential groove.

13. The retractable syringe needle of claim 10, wherein the rigid ring has a longitudinal ridge on the interior surface of the ring, said longitudinal ridge being adapted to fit into the open end of the longitudinal slot.

14. The retractable syringe needle of claim 1, comprising a first means for releasably engaging the pin at a first defined location in said longitudinal slot so as to hold said needle assembly in said second position; a second means for releasably engaging the pin at a second defined location in said longitudinal slot so as to hold said needle assembly in said first position; and a third means for irreversibly engaging the pin at the second defined location in said longitudinal slot so as to hold said needle assembly in said first position.

15. The retractable syringe needle of claim 14, wherein the first means for releasably engaging the pin at a first defined location in said longitudinal slot so as to hold said needle assembly in said second position comprises a first notch which intersects said longitudinal slot at said first defined location; and wherein the second means for releasably engaging the pin at a second defined location in said longitudinal slot so as to hold said needle assembly in said first position comprises a second notch which intersects said longitudinal slot at said second defined location, said first and second notches each being wide enough to receive the pin engaged by the longitudinal slot.

16. The retractable syringe needle of claim 15, wherein the third means for irreversibly engaging the pin at the second defined location in said longitudinal slot so as to hold said needle assembly in said first position comprises a third notch which intersects said longitudinal slot at said second defined location, where the third notch and the second notch extend in opposite directions from the longitudinal slot, and where the third notch is wide enough to receive the pin engaged by the longitudinal slot, and where the third notch comprises a means for irreversibly locking the pin into position.

17. The retractable syringe needle of claim 16, wherein the means for irreversibly locking the pin into position comprises a pair of flexible projections extending from opposite sides of the third notch, said projections having tips which contact each other; said tips being adapted to allow the pin engaged by the slot to pass therethrough when the pin enters the third notch from the longitudinal slot, and to not allow the pin to pass therethrough to exit the third notch.

18. The retractable syringe needle of claim 17, wherein said each of the flexible projections makes an acute angle with the wall of the notch from which it projects, and wherein each of the flexible projections is directed away from the longitudinal slot.

19. The retractable syringe needle of claim 10, additionally comprising a first means for releasably engaging the pin at a first defined location in said longitudinal slot so as to hold said needle assembly in said second position; a second means for releasably engaging the pin at a second defined location in said longitudinal slot so as to hold said needle assembly in said first position; and a means for irreversibly engaging the pin at the second defined location in said longitudinal slot so as to hold said needle assembly in said first position.

20. The retractable syringe needle of claim 19, wherein the first means for releasably engaging the pin at a first defined location in said longitudinal slot so as to hold said needle assembly in said second position comprises a first notch which intersects said longitudinal slot at said first defined location;

wherein the second means for releasably engaging the pin at a second defined location in said longitudinal slot so as to hold said needle assembly in said first position comprises a second notch which intersects said longitudinal slot at said second defined location; and wherein the means for irreversibly engaging the pin comprises the rigid ring; a rigid tongue attached to the first end of the rigid ring by a living hinge, where the second end of the rigid ring is substantially flush with one side of the second notch; and a means for folding the rigid tongue against an external surface of the ring and irreversibly securing it against the external surface of the ring so that the end of the rigid tongue blocks the opening of the second notch; said first and second notches each being wide enough to receive the pin engaged by the longitudinal slot.

21. The retractable syringe needle of claim 20, wherein a post on the rigid tongue irreversibly snaps into a hole in the external surface of the rigid ring.

22. The retractable syringe needle of claim 20, wherein a hook on the rigid tongue irreversibly snaps around the second end of the rigid ring.

23. A retractable syringe assembly, comprising:
a) a tubular syringe barrel having a defined outer diameter, said barrel having an open end adapted to receive the plunger and a closed end having a tip projecting therefrom,
said tip having a maximum defined diameter which is less than the defined outer diameter of the syringe barrel and a longitudinal bore passing through the tip and the closed end of the barrel,
b) a plunger slidably positioned within the syringe barrel; and
c) a retractable syringe needle, said retractable syringe needle comprising:
i) a needle assembly featuring:
a needle-holding mechanism, said needle-holding mechanism comprising a hub and an annular sleeve connected with said hub, said sleeve having an exterior surface and an interior surface, where said interior surface of said sleeve defines a cavity having a diameter which is substantially equal to the maximum defined diameter of the tip of the syringe barrel, the interior surface of the sleeve being adapted to frictionally engage the tip of the syringe barrel;
a hypodermic needle extending through said hub; and
a pin directly connected to the exterior surface of said annular sleeve;
ii) a container with a defined cylindrical axis having a tubular wall with a longitudinal slot therein, said container having a first open end adapted to receive a syringe barrel and a second open end adapted to receive a syringe needle, said container having said needle assembly mounted therein so that the pin is slidably engaged by the longitudinal slot, and so that said needle assembly may be moved from a first position where the needle is within the container to a second position where the needle is exposed by sliding the pin toward the second open end of the container and causing the needle to pass through the second open end;

iii) a means for biasing the needle assembly toward said first position; and iv) a means for releasably engaging the pin at a defined location in said longitudinal slot so as to hold said needle assembly in said second position; wherein said means for releasably engaging the pin comprises a notch which intersects said longitudinal slot at said defined location, so that said needle assembly may be releasably held in said second position by sliding said pin out of said longitudinal slot into said notch;

wherein the notch is selected from the group consisting of a straight notch which is transverse to the longitudinal slot, a T-shaped slot, a C-shaped slot, and an L-shaped slot; and wherein the hub of said needle-holding mechanism is movably positioned along the defined cylindrical axis of the container, the position of the hub being maintained along the axis by a crosspiece rigidly fixed to a defined location along the length of the pin, said crosspiece being on the exterior of the container, and being unable to pass through the longitudinal slot.

24. A retractable syringe needle for use with a syringe, said syringe comprising a plunger and a tubular syringe barrel having a defined outer diameter, said barrel having an open end adapted to receive the plunger and a closed end having a tip projecting therefrom, said tip having a maximum defined diameter which is less than the defined outer diameter of the syringe barrel and a longitudinal bore passing through the tip and the closed end of the barrel, said retractable syringe needle being made by a process comprising the steps of:

a) obtaining a needle assembly comprising:

a needle-holding mechanism, said needle-holding mechanism comprising a hub and an annular sleeve connected with said hub, said sleeve having an exterior surface and an interior surface, where said interior surface of said sleeve defines a cavity having a diameter which is substantially equal to the diameter of the tip of the syringe barrel, the interior surface of the sleeve being adapted to frictionally engage the tip of the syringe barrel;

a hypodermic needle extending through said hub; and a pin directly connected to the exterior surface of said annular sleeve;

b) obtaining a container with a defined cylindrical axis having a tubular wall with a longitudinal slot therein, said container having a first open end adapted to receive a syringe barrel and a second open end adapted to receive a syringe needle, where the longitudinal slot has an open end at the first open end of the container and a closed end at the second open end of the container;

c) inserting a biasing means into the container;

d) mounting said needle assembly in the container so that the pin is slidably engaged by the longitudinal slot, and so that said biasing means reversibly biases the needle assembly toward a first position where the needle is concealed within the container;

wherein said longitudinal slot comprises a means for releasably engaging the pin in a second position where the needle is exposed, said releasable engaging means comprising a notch which intersects said longitudinal slot at said defined location, so that said needle assembly may be releasably held in said second position by sliding said pin out of said longitudinal slot into said notch;

wherein the notch is selected from the group consisting of a straight notch which is transverse to the longitudinal slot, a T-shaped slot, a C-shaped slot, and an L-shaped slot; and wherein the hub of said needle-holding mechanism is movably positioned along the defined cylindrical axis of the container, the position of the hub being maintained along the axis by a crosspiece rigidly fixed to a defined location along the length of the pin, said crosspiece being on the exterior of the container, and being unable to pass through the longitudinal slot.

25. A double-ended safety needle, comprising:

a) a needle assembly featuring a hub, a hollow straight needle, and a pin connected with said hub; where the needle extends through the hub so as to expose a first end of the needle projecting in a first direction and a second end of the needle projecting in a second direction;

b) a container with a defined cylindrical axis having a tubular wall with a first longitudinal slot therein, said container having a first open end adapted to receive a receptacle for venous blood and a second open end adapted to receive the hollow needle, said container having said needle assembly mounted therein so that (i) the first end of the needle is directed toward the second open end of the container, and (ii) the pin on the needle assembly is slidably engaged by the first longitudinal slot;

where said needle assembly may be moved from a first position where the needle is within the container to a second position where the first end of the needle is exposed by sliding the pin toward the second open end of the container and causing the first end of the needle to pass through the second open end;

c) a means for biasing the needle assembly toward said first position;

d) a first means for releasably engaging the pin at a first defined location in said first longitudinal slot so as to hold said needle assembly in said second position;

e) a second means for releasably engaging the pin at a second defined location in said first longitudinal slot so as to hold said needle assembly in said first position; and f) a means for irreversibly engaging the pin at said second defined location in said first longitudinal slot;

where the hub of said needle-holding mechanism is movably positioned along the defined cylindrical axis of the container, the position of the hub being maintained along the axis of the container by a crosspiece rigidly fixed to a defined location along the length of the pin, said crosspiece being on the exterior of the container, and being unable to pass through the first longitudinal slot.

26. The double-ended safety needle of claim 25, wherein the longitudinal slot extends from the first open end of the container to a defined point near the second open end of the container, said longitudinal slot being open-ended at the first open end of the container and closed at the second open end of the container; said syringe needle additionally comprising a rigid ring having a first end and a second end; where the rigid ring is positioned over the first open end of the container so as to close the open end of the longitudinal slot.

27. The double-ended safety needle needle of claim 26, wherein the first means for releasably engaging the pin at a first defined location in said longitudinal slot so as to hold said needle assembly in said second position comprises a first notch which intersects said longitudinal slot at said first defined location; and wherein the second means for releasably engaging the pin at a second defined location in said longitudinal slot so as to hold said needle assembly in said first position comprises a second notch which intersects said longitudinal slot at said second defined location, said first and second notches each being wide enough to receive the pin engaged by the longitudinal slot.

28. The double-ended safety needle needle of claim 27, wherein the means for irreversibly engaging the pin at the second defined location in said longitudinal slot so as to hold said needle assembly in said first position comprises a third notch which intersects said longitudinal slot at said second defined location, where the third notch and the second notch extend in opposite directions from the longitudinal slot, and where the third notch is wide enough to receive the pin engaged by the longitudinal slot, and where the third notch comprises a means for irreversibly locking the pin into position.

29. The double-ended safety needle needle of claim 28, wherein the means for irreversibly locking the pin into position comprises a pair of flexible projections extending from opposite sides of the third notch, said projections having tips which contact each other; said tips being adapted to allow the pin engaged by the slot to pass therethrough when the pin enters the third notch from the longitudinal slot, and to not allow the pin to pass therethrough to exit the third notch.

30. The double-ended safety needle of claim 27, wherein the means for irreversibly engaging the pin comprises the rigid ring; a rigid tongue attached to the first end of the rigid ring by a living hinge, where the second end of the rigid ring is substantially flush with one side of the second notch; and a means for folding the rigid tongue against an external surface of the ring and irreversibly securing it against the external surface of the ring so that the end of the rigid tongue blocks the opening of the second notch.

31. The double-ended safety needle of claim 26, wherein a circumferential ridge on the interior surface of the rigid ring snaps into a circumferential groove on the exterior surface of the container.

32. The double-ended safety needle of claim 26, further comprising a plurality of circumferential strengthening ridges on the exterior surface of the container.

33. A retractable needle for use with a catheter, comprising:
   a) a needle assembly featuring:
      a cylindrical hub having a posterior end and an anterior end;
      a hollow needle extending through said hub and projecting from the anterior end of the hub;
      a hollow, cylindrically symmetric flash chamber having a first end which is connected in a leakproof fashion with the posterior end of the hub, and a sealed second end; and
      a pin having a defined diameter connected with the hub, said pin having a crosspiece rigidly connected to a defined location along the length of the pin;
      where an interior of said hollow needle is in fluid communication with the interior of the flash chamber;
   b) a container with a defined cylindrical axis having a tubular wall with a longitudinal slot therein, said container having a first end adapted to allow the hollow needle to pass therethrough and a closed second end; said container having said needle assembly mounted therein so that the pin is slidably engaged by the longitudinal slot, and so that said needle assembly may be moved from a first position where the needle is within the container to a second position where the needle is exposed by sliding the pin toward the first end of the container;
   c) a means for releasably engaging the pin at a first defined location in said longitudinal slot so that the needle assembly is held in said first position;
   d) a means for releasably engaging the pin at a second defined location in said longitudinal slot so that the needle assembly is held in said second position;
   e) a means for irreversibly engaging the pin at said first defined location in said longitudinal slot so that the needle assembly is held in said first position;
   f) a catheter which is supported by the needle when the needle assembly is in the second position; and
   g) a means for removably fastening the catheter to the first end of the housing;
      wherein the hub of said needle-holding mechanism is movably positioned along the cylindrical axis of the container, the position of the hub being maintained along the axis by a crosspiece rigidly fixed to a defined location along the length of the pin, said crosspiece being on the exterior of the container, and being unable to pass through the longitudinal slot.

34. The retractable syringe needle of claim 33, wherein the first means for releasably engaging the pin at a first defined location in said longitudinal slot so as to hold said needle assembly in said second position comprises a first notch which intersects said longitudinal slot at said first defined location; and wherein the second means for releasably engaging the pin at a second defined location in said longitudinal slot so as to hold said needle assembly in said first position comprises a second notch which intersects said longitudinal slot at said second defined location, said first and second notches each being wide enough to receive the pin engaged by the longitudinal slot.

35. The retractable syringe needle of claim 34, wherein the means for irreversibly engaging the pin at the second defined location in said longitudinal slot so as to hold said needle assembly in said first position comprises a third notch which intersects said longitudinal slot at said second defined location, where the third notch and the second notch extend in opposite directions from the longitudinal slot, and where the third notch is wide enough to receive the pin engaged by the longitudinal slot, and where the third notch comprises a means for irreversibly locking the pin into position.

36. The retractable syringe needle of claim 35, wherein the means for irreversibly locking the pin into position comprises a pair of flexible projections extending from opposite sides of the third notch, said projections having tips which contact each other; said tips being adapted to allow the pin engaged by the slot to pass therethrough when the pin enters the third notch from the longitudinal slot, and to not allow the pin to pass therethrough to exit the third notch.

37. The retractable syringe needle of claim 34, wherein the container comprises a housing having a first open end adapted to admit the needle assembly and a second open end adapted to admit the hollow needle, and a cap which closes the first open end of the housing, and wherein the longitudinal slot in the housing extends from the first open end of the housing to a defined point near the second open end of the container, said longitudinal slot being open-ended at the first open end of the container and closed at the second open end of the container;

wherein said cap has a skirt that extends over the exterior of the housing until it reaches the edge of the first notch; and wherein the means for irreversibly engaging the pin comprises the cap; a rigid tongue attached to the cap by a living hinge; and a means for folding the rigid tongue against the skirt of the cap and irreversibly securing it against the external surface of the skirt so that the end of the rigid tongue blocks the opening of the second notch.

38. A disposable hypodermic syringe needle for use with a syringe, said syringe comprising a plunger and a tubular syringe barrel having a defined outer diameter, said barrel having an open end adapted to receive the plunger and a closed end having a tip projecting therefrom, said tip having a maximum defined diameter which is less than the defined outer diameter of the syringe barrel and a longitudinal bore passing through the tip and the closed end of the barrel, said hypodermic syringe needle being manufactured by a method comprising the steps of:

a) obtaining a syringe needle assembly, said syringe needle assembly comprising a needle-holding mechanism, said needle-holding mechanism comprising a hub and an annular sleeve connected with said hub, said sleeve having an exterior surface and an interior surface, where said interior surface of said sleeve defines a cavity having a diameter which is substantially equal to the diameter of the tip of the syringe barrel, the interior surface of the sleeve being adapted to frictionally engage the tip of the syringe barrel; a hypodermic needle extending through said hub; a pin directly connected to the exterior surface of said annular sleeve; and a spring having a first end which engages said hub and a second end;

b) obtaining an anterior container portion having a first tubular wall, said anterior container portion having a first open end adapted to receive a syringe barrel, a second open end adapted to receive a hypodermic needle, a ridge on the interior surface of said first tubular wall which prevents the syringe barrel from passing through the second end of the anterior container portion, a first longitudinal slot through the first tubular wall, and a means of releasably engagng said pin at said first defined point; where said first longitudinal slot is adapted to receive said pin; and where said first longitudinal slot runs from the first end of the anterior container portion to a first defined point near the second end of the anterior container portion;

c) obtaining a posterior container portion having a second tubular wall adapted to receive a syringe barrel, said posterior container portion having a first open end, a second open end, and a second longitudinal slot through the second tubular wall; where said second longitudinal slot is adapted to receive said pin; and where said second longitudinal slot runs from the first end of the posterior container portion to a defined point near the second end of the posterior container portion;

d) positioning said syringe needle assembly within the posterior container portion so that the second longitudinal slot slidably engages said pin, and e) adjoining the first end of the anterior container portion to the first end of the posterior container portion to form a tubular container so that (i) the first and second longitudinal slots cooperate to form a third slot which slidably engages the pin; and so that (ii) the second end of the spring engages the ridge on the interior surface of said first tubular wall, biasing the hub of the syringe needle assembly away from the second end of the anterior container portion so that the needle is contained within the container, while allowing the needle to emerge through the opening in the anterior portion of the chamber when the spring is compressed.

39. A retractable syringe needle for use with a syringe, said syringe comprising a plunger and a tubular syringe barrel having a defined outer diameter, said barrel having an open end adapted to receive the plunger and a closed end having a tip projecting therefrom, said tip having a defined diameter which is less than the defined outer diameter of the syringe barrel and a longitudinal bore passing through the tip and the closed end of the barrel, said retractable syringe needle comprising:

a) a needle assembly featuring:
a needle-holding mechanism, said needle-holding mechanism comprising a hub and an annular sleeve connected with said hub, said sleeve having an exterior surface and an interior surface, where said interior surface of said sleeve defines a cavity having a diameter which is substantially equal to the diameter of the tip of the syringe barrel, the interior surface of the sleeve being adapted to frictionally engage the tip of the syringe barrel;
a hypodermic needle extending through said hub; and
a pin directly connected to the exterior surface of said annular sleeve;

b) a container with a defined cylindrical axis having a tubular wall with a longitudinal slot therein, said container having a first open end adapted to receive a syringe barrel and a second open end adapted to receive a syringe needle, said container having said needle assembly mounted therein so that the pin is slidably engaged by the longitudinal slot, and so that said needle assembly may be moved from a first position where the needle is within the container to a second position where the needle is exposed by sliding the pin toward the second open end of the container and causing the needle to pass through the second open end;

c) a means for biasing the needle assembly toward said first position; and d) a means for releasably engaging the pin at a defined location in said longitudinal slot so as to hold said needle assembly in said second position;
wherein the hub of said needle-holding mechanism is movably positioned along the defined cylindrical axis of the container, the position of the hub being maintained along the axis by a crosspiece rigidly fixed to a defined location along the length of the pin, said crosspiece being on the exterior of the container, and being unable to pass through the longitudinal slot; and
wherein the interior surface of the sleeve defines a cylindrical cavity of constant diameter, said sleeve being adapted to frictionally engage the cylindrical tip of the syringe barrel, said cylindrical tip having a constant diameter.

40. A retractable needle, comprising:
a) a hollow hypodermic needle;
b) a cylindrical hub having an axial passage therethrough, the hollow needle being connected with the hub so that the axial passage and the interior of the hollow needle form a continuous conduit;

c) an adjustable-length tube having a first end and a second end, said tube having a length which may be reversibly altered from a first contracted length to a second extended length;

d) a means for reversibly securing a tip of a syringe barrel to the first end of the adjustable-length tube so that the interior of the syringe barrel is in fluid communication with the interior of the adjustable-length tube;

e) a means for reversibly securing a tip of the cylindrical hub to the second end of the adjustable-length tube so that the interior of the hollow needle is in fluid communication with the interior of the adjustable-length tube;

f) a tubular sheath disposed around the adjustable-length tube, said tubular sheath having a first end which is rigidly connected with the first end of the adjustable-length tube and a second end having an opening which is large enough to allow the end of the hollow needle to pass therethrough; and g) a means to alter the length of the adjustable-length tube from the contracted length to the extended length, said length-altering means comprising:

a longitudinal slot running along the length of the tubular sheath;

a knob slidably engaging said longitudinal slot, said knob being rigidly connected with the second end of the adjustable length tube;

a means for reversibly securing the knob at a first position along the length of the longitudinal slot, where the tube is contracted when the knob is in said first position;

a means for reversibly securing the knob at a second position along the length of the longitudinal slot, where the tube is extended when the knob is in said first position;

a means for irreversibly securing the knob at said first position along the length of the longitudinal slot; and a means for reversibly sliding the knob from the first position to the second position;

where the hollow needle is entirely disposed within the sheath when the adjustable-length tube is contracted, and where the end of the hollow needle is exposed through the opening in the second end of the sheath when the adjustable-length tube is extended.

41. The retractable syringe needle of claim 40, wherein the tip of the syringe barrel is frusto-conical, and the first end of the adjustable-length tube features a frusto-conical female joint which frictionally engages the tip of the syringe barrel.

42. The retractable syringe needle of claim 40, wherein the tip of the syringe barrel is cylindrical and has a constant diameter, and the first end of the adjustable-length tube features a cylindrical female joint of constant diameter which frictionally engages the tip of the syringe barrel.

* * * * *